United States Patent
Marino

(10) Patent No.: US 12,156,959 B2
(45) Date of Patent: Dec. 3, 2024

(54) EXTRACORPOREAL DEVICES FOR METHODS FOR TREATING DISEASES ASSOCIATED WITH ANTI-NEUTROPHIL CYTOPLASMIC ANTIBODIES

(71) Applicant: GAMBRO LUNDIA AB, Lund (SE)

(72) Inventor: Stephen F. Marino, Berlin (DE)

(73) Assignee: GAMBRO LUNDIA AB, Lund (SE)

( * ) Notice: Subject to any disclaimer, the term of this patent is extended or adjusted under 35 U.S.C. 154(b) by 792 days.

(21) Appl. No.: 17/414,359

(22) PCT Filed: Dec. 20, 2019

(86) PCT No.: PCT/EP2019/086676
§ 371 (c)(1),
(2) Date: Jun. 16, 2021

(87) PCT Pub. No.: WO2020/127969
PCT Pub. Date: Jun. 25, 2020

(65) Prior Publication Data
US 2022/0088279 A1    Mar. 24, 2022

(30) Foreign Application Priority Data
Dec. 20, 2018   (EP) .................................... 18214369

(51) Int. Cl.
*A61M 1/34*        (2006.01)
*A61K 38/00*       (2006.01)
(Continued)

(52) U.S. Cl.
CPC ........... *A61M 1/3486* (2014.02); *A61K 38/00* (2013.01); *A61K 38/482* (2013.01);
(Continued)

(58) Field of Classification Search
None
See application file for complete search history.

(56) References Cited

U.S. PATENT DOCUMENTS

| | | | | | |
|---|---|---|---|---|---|
| 4,608,253 | A | * | 8/1986 | Ohnishi | ............... B01J 20/3248 424/94.66 |
| 5,650,288 | A | * | 7/1997 | MacFarlane | ....... G01N 33/9493 435/23 |

(Continued)

FOREIGN PATENT DOCUMENTS

| CN | 101087807 A | 12/2007 |
|---|---|---|
| CN | 108611343 A | 10/2018 |

OTHER PUBLICATIONS

PCT Search Report and Written Opinion prepared for PCT/EP2019/086676, completed Feb. 25, 2018.
(Continued)

*Primary Examiner* — Manuel A Mendez
(74) *Attorney, Agent, or Firm* — Barnes & Thornburg LLP

(57) ABSTRACT

The invention relates to a blood treatment device configured to remove anti-neutrophil cytoplasmic antibodies (ANCAs) from the blood or blood plasma of a person in need thereof in an extracorporeal blood circuit, wherein the device comprises a matrix, and wherein said matrix comprises a monomeric form of proteinase 3 (PR3). The invention further relates to an extra-corporeal blood circuit comprising a blood treatment device of the invention and to the blood treatment device for use as a medicament or to methods of treating a medical condition associated with ANCA.

Figure 1:
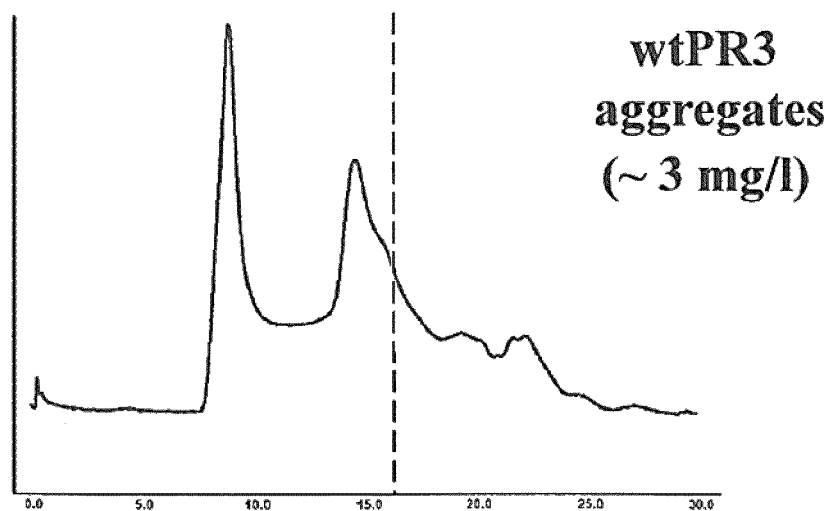
Figure 1:
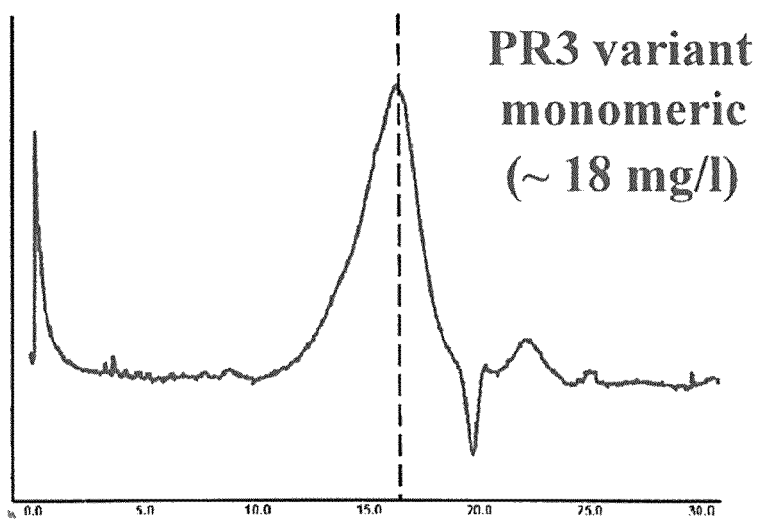

24 Claims, 5 Drawing Sheets
Specification includes a Sequence Listing.

(51) Int. Cl.
    *A61K 38/48* (2006.01)
    *A61K 39/385* (2006.01)
    *A61K 47/50* (2017.01)
    *A61K 47/68* (2017.01)
    *A61K 47/69* (2017.01)

(52) U.S. Cl.
    CPC ............ *A61K 39/385* (2013.01); *A61K 47/50* (2017.08); *A61K 47/6849* (2017.08); *A61K 47/6957* (2017.08); *A61M 2202/0445* (2013.01); *C07K 2317/92* (2013.01)

(56) References Cited

U.S. PATENT DOCUMENTS

| | | | | |
|---|---|---|---|---|
| 2014/0161899 | A1* | 6/2014 | Schulte | A61K 35/16 424/530 |
| 2022/0054731 | A1* | 2/2022 | Cooney | A61M 1/3687 |

OTHER PUBLICATIONS

Schneidewind, Jana-Maria, et al., "PR3 ANCA-positive vasculitis (Wegener's granulomatosis) treated by Immunoadsorption in failed drug therapies." 2000, Journal of the American Society of Nephrology, vol. 11, Nr: Program and Abstract Issue, p. 97A.

Reiners, Katrin S., et al., "Selective killing of B-cell hybridomas targeting proteinase 3, Wegener's autoantigen," 2004, Immunology, vol. 112, Nr: 2, pp. 228-236.

Lee, A. S., et al., "A novel capture-ELISA for detection of anti-neutrophil cytoplasmic antibodies (ANCA) based on c- myc peptide recognition in carboxy-terminally tagged recombinant neutrophil serine proteases," 2005, Journal of Immunological Methods, vol. 307, Nr: 1-2, pp. 62-72.

English Translation of Chinese Office Action issued for Application No. 2019800853132, mailed Dec. 27, 2023.

\* cited by examiner (A)

(B)

(A)

(B)

(A)

(B)

(A)

Epoxy resin → Covalently immobilized target protein

(B)

Amino resin → Covalently immobilized target protein

EXTRACORPOREAL DEVICES FOR METHODS FOR TREATING DISEASES ASSOCIATED WITH ANTI-NEUTROPHIL CYTOPLASMIC ANTIBODIES

CROSS-REFERENCE TO RELATED APPLICATIONS

This application is a national stage entry under 35 U.S.C. § 371(b) of PCT International Application No. PCT/2019/086676, filed Dec. 20, 2019, which claims the benefit of European Patent Application Serial No. 18214369.3, filed on Dec. 20, 2018, the entire disclosure of both of which are incorporated herein by reference.

DESCRIPTION

The invention relates to the field of extracorporeal removal of anti-neutrophil cytoplasmic antibodies (ANCAs) from the blood or blood plasma of a patient and related devices.

The invention relates to a blood treatment device configured to remove anti-neutrophil cytoplasmic antibodies (ANCAs) from the blood or blood plasma of a person in need thereof in an extracorporeal blood circuit, wherein the device comprises a matrix, and wherein said matrix comprises a monomeric form of proteinase 3 (PR3). The invention further relates to an extracorporeal blood circuit comprising a blood treatment device of the invention and to the blood treatment device for use as a medicament or to methods of treating a medical condition associated with ANCA.

BACKGROUND OF THE INVENTION

A fundamental constituent of the human immune system comprises antibody molecules (immunoglobulins) that freely circulate in the bloodstream. These antibodies, primarily immunoglobulin type G (IgG), are produced by B cells that have been previously exposed to target molecules, antigens, that have been identified as "foreign" to the body. Antibody molecules have two functional parts, namely antigen binding sites that are tailored for binding to a specific target, and an effector part, that can be thought of as a tag and can be recognized by other components of the immune system which then destroy the target to which the antibody is bound.

The process of B cell activation and optimization of antibodies has evolved to eliminate B cells producing antibody molecules that can recognize antigens present in a patient's own body, so-called "self-antigens"; this normally prevents the immune system from mounting an attack on the body itself. However, there is a number of diseases that are indeed caused by such antibodies directed to self-antigens, often referred to as autoantibodies. It is presently not clear why some B cells activated by self-antigens escape elimination, but the results can be severe. In patients having such autoimmune diseases, the immune system mounts an attack on the body's own molecules, resulting in tissue damage that can produce severe disability or death. In a group of autoimmune diseases, often referred to as ANCA-(anti-neutrophil cytoplasmic antibodies) associated vasculitides (AAVs), auto-antibodies are produced that can bind to antigens that exist on the surfaces of neutrophil granulocytes (Thieblemont, N. et al, (2016) Seminars in Immunology 28: 159-173).

Neutrophils are the most abundant white blood cells (comprising 40-70% of the total leucocyte pool) and represent the first line of defense against pathogens at sites of injury and large surface area mucous membrane exposure (for example, in the lungs) to the outside. They can identify and destroy pathogenic organisms in several ways, including by the controlled release of cytotoxic proteins and peptides stored in intracellular membrane bound structures called granules. The fusion of these granules with the plasma membrane—and concomitant release of their cytotoxic contents, a process called degranulation—is normally a strictly controlled and localized process. Toxins are released into the environment around neutrophils that have been "activated" by recognition of pathogens. These cytotoxins are intended to kill the recognized organism(s) but cause damage to healthy surrounding tissue as well.

In the case of ANCA vasculitis patients, ANCAs binding to antigens on the neutrophil surface activate the neutrophils for degranulation even without recognition of pathogenic or foreign antigens. This uncontrolled degranulation can happen anywhere in the body where ANCAs meet neutrophils and the resulting cytotoxin release causes systemic tissue damage that primarily affects small blood vessels. Organs like the skin, lungs and kidneys—which contain a profusion of small vessels—suffer severe damage leading to their failure and, ultimately, the death of the patient.

Given that ANCAs are the causative agent in these diseases, standard therapy aims to reduce the immunoglobulin concentration in the blood. This is typically achieved via administration of immunosuppressing drugs and/or non-specific targeting of the patient's antibody producing B cells (Luqmani, R A (2014) Frontiers in immunology 5:1-9). While such treatment is effective for temporary symptom alleviation it is decidedly nonspecific: the treatment induces general immune suppression including a decrease in all immunoglobulin levels and thus decimates the patient's humoral immunity. The majority of ANCA patients consequently suffers or even die of infections due to a compromised immune system.

In cases of severe disease, patients undergo a procedure called plasmapheresis in which the entire liquid portion of the blood, the plasma, is separated from the blood cells outside of the body and discarded. The separated cells are retained, mixed with a plasma substitute and reinfused. This treatment also effectively eliminates the pathogenic immunoglobulins from the blood, but at great expense: all immunoglobulins and other beneficial substances in the patient's plasma are eliminated. This also leads to a temporary alleviation of the disease symptoms but again at the cost of the humoral immunity, with the added risk of infection and allergic reaction to the components of the plasma substitution fluid.

In light of the means established in the prior art it is apparent that a more selective procedure, i.e. the specific targeting of only the pathogenic antibodies (ANCAs), would be of great benefit to AAV patients. Specific procedures would eliminate only the disease-causing ANCAs while leaving the remaining immunoglobulin complement and the patient's humoral immunity intact. Such a procedure would also bring no increased risk of allergic reaction/infection. Specific removal of pathogenic autoantibodies would be expected to not only improve the effect of the standard treatments but perhaps also to potentiate less stringent immune suppressive regimens, thereby preserving patient's native immune system function for longer periods and correspondingly reducing auxiliary treatment/deaths due to infection.

One of the most common ANCA antigens is the serine protease proteinase 3 (PR3). PR3 is a granule component but it is also found adhering to the outside of the neutrophil plasma membrane—hence its accessibility to PR3-ANCAs. For example, IgG class ANCA directed to proteinase 3 (PR3) of neutrophils and monocytes seem to be directly involved in the pathophysiology of vascular damage by causing excessive neutrophil activation and vessel wall destruction. It is now recognized that PR3-ANCA is found in about 80% of patients with Wegener's granulomatosis, and also in about 35% of patients with microscopic polyangiitis, Churg-Strauss syndrome, and renal-limited rapidly progressive glomerulonephritis (Wiik A. (2000) Arthritis Res 2(4):252-254).

In solution, PR3 exists as large and heterogeneous oligomeric species and is prone to precipitation (Jerke, U., et al (2017) Scientific Reports 7:43328). Furthermore, multiple difficulties have been experienced with PR3 when attempting to develop PR3-based capture reagents for ANCA autoantibodies in the field of ELISA diagnostics. For example, conformational changes of the PR3 molecule, resulting from mutagenesis, variable intracellular processing, or purification procedures, can affect its recognition by ANCA autoantibodies, therefore reducing the applicability of PR3 proteins in capturing, either for detecting or depleting, PR3 ANCA autoantibodies.

Considering the difficulties outlined above, there exists a significant need in the field of treating ANCA-associated medical conditions to develop improved means for selective removal of pathogenic PR3 autoantibodies.

BRIEF DESCRIPTIONS OF THE DRAWINGS

The invention is further described by the following figures. They are intended to represent a more detailed illustration of a number of preferred non-limiting embodiments or aspects of the invention without limiting the scope of the invention described herein.

FIGS. 1A-1B show a comparison of wtPR3 and monomeric PR3 properties by size exclusion chromatography. Specifically, FIG. 1A shows a size exclusion chromatogram (S200) with the elution profile of wtPR3. The protein does not elute in a discrete peak but rather as a collection of large aggregates with approximate sizes ranging from monomeric (ca. 26 kD) to over 600 kD. FIG. 1B shows the analogous chromatogram of a monomeric Trp222Ala PR3 variant showing a more uniform elution primarily at the predicted retention time of a monomeric species.

Figure 2:
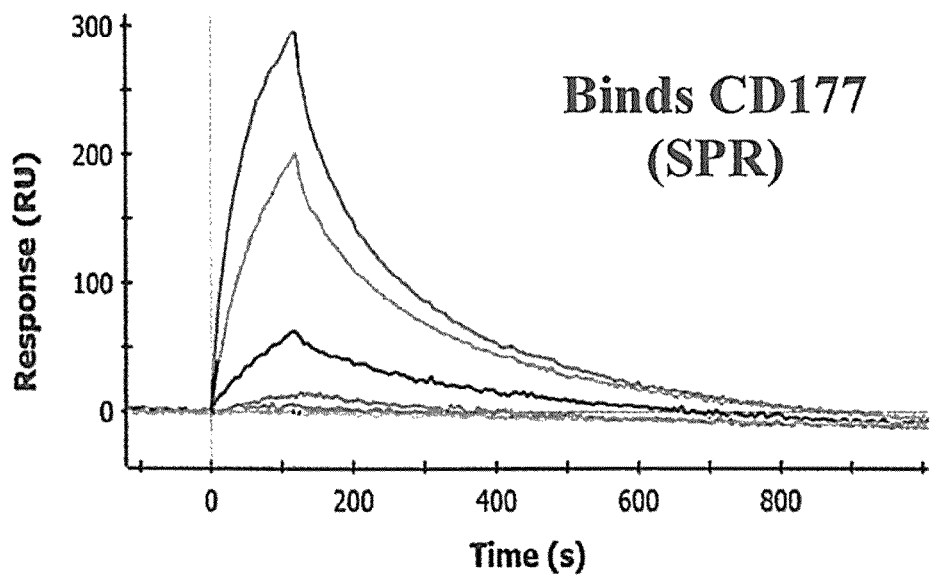
Figure 2:
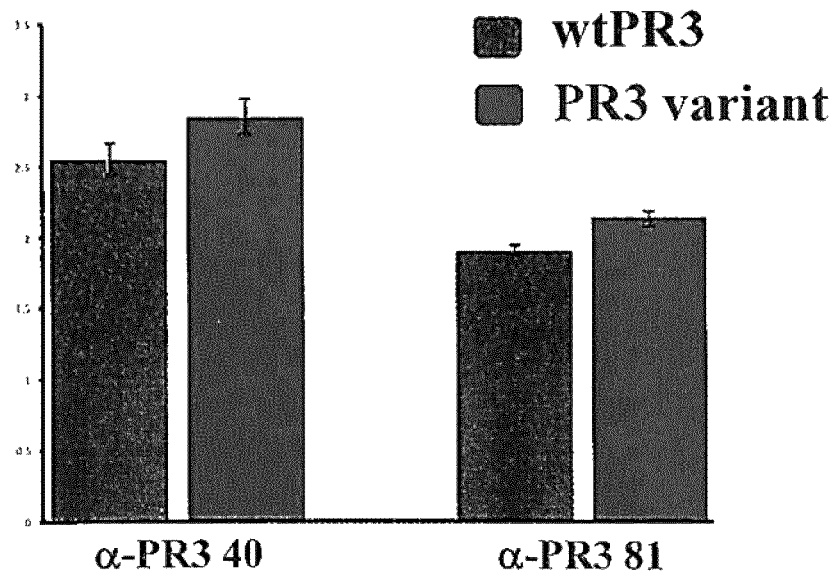

FIGS. 2A-2B show a comparison of wtPR3 and monomeric PR3 properties by SPR and ELISA. FIG. 2A shows a raw SPR sensorgram of the binding interaction of a concentration series of soluble monomeric Trp222Ala PR3 variant to immobilized CD177. The affinity of the interaction was measured to be $5.7 \times 10^{-8}$ M. FIG. 2B shows an ELISA assay using two different anti-PR3 antibodies (anti-PR3 40 and anti-PR3 81) purified from hybridoma supernatants. The antibodies each recognize distinct, non-overlapping epitopes on PR3. wtPR3 (left bar) and the monomeric Trp222Ala PR3 variant (right bar) are equally well recognized by the antibodies.

Figure 3:
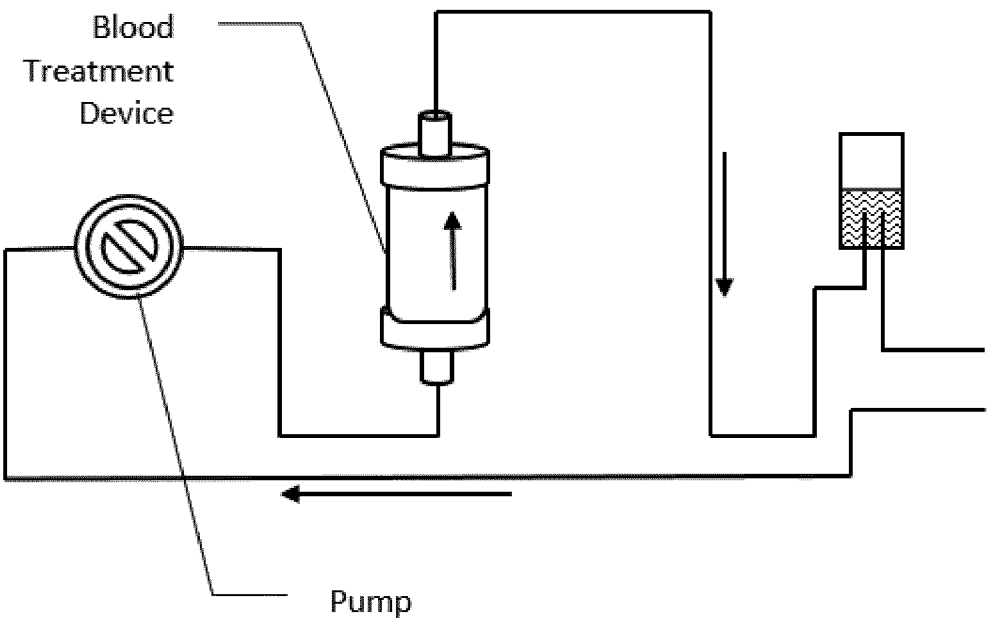

FIG. 3 shows a schematic representation of an extracorporeal treatment circuit comprising a blood treatment device. The device can be a cartridge or filter comprising a membrane, resin or non-woven based support to which a ligand having affinity for a target protein has been bound. The circuit can be operated in hemoperfusion mode. In cases where the blood treatment device is a hollow fiber membrane filter device the treatment mode can be hemodialysis, hemodiafiltration, hemofiltration or hemoperfusion of the filter with closed dialysate/filtrate ports.

Figure 4:
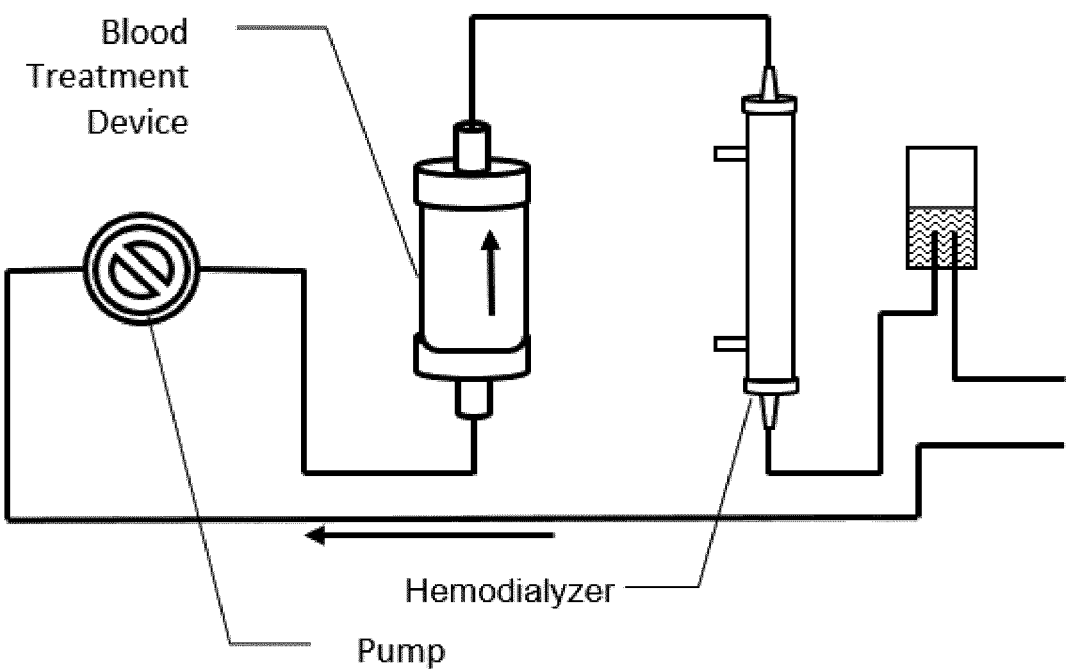
Figure 4:
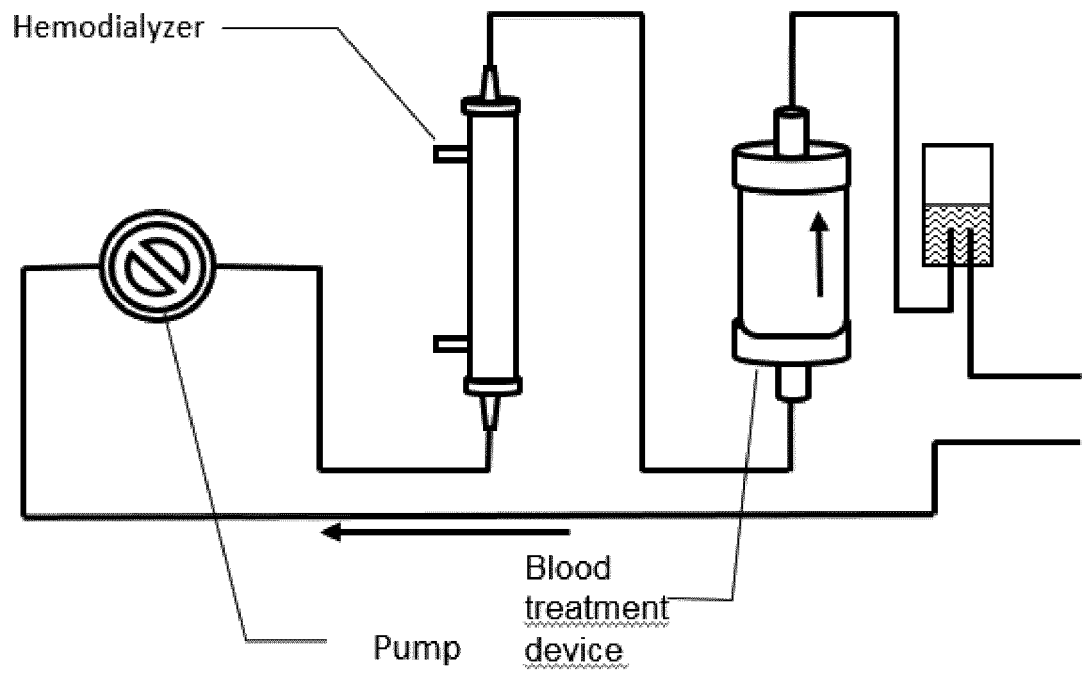

FIGS. 4A-4B show a schematic representation of an extracorporeal treatment circuit comprising a blood treatment device. The device can be an adsorption cartridge comprising a resin or non-woven or a filter comprising a membrane, to which a ligand having affinity for a target protein has been bound, respectively. The blood treatment device can be located upstream of a hemodialyzer (pre-dialyzer setting, as shown in FIG. 4A) or downstream of a hemodialyzer (post-dialyzer setting, as shown in FIG. 4B). The non-functionalized hemodialyzer in the circuit can be operated in different treatment modes depending on the medical need, including hemodialysis, hemodiafiltration or hemofiltration mode.

Figure 5:
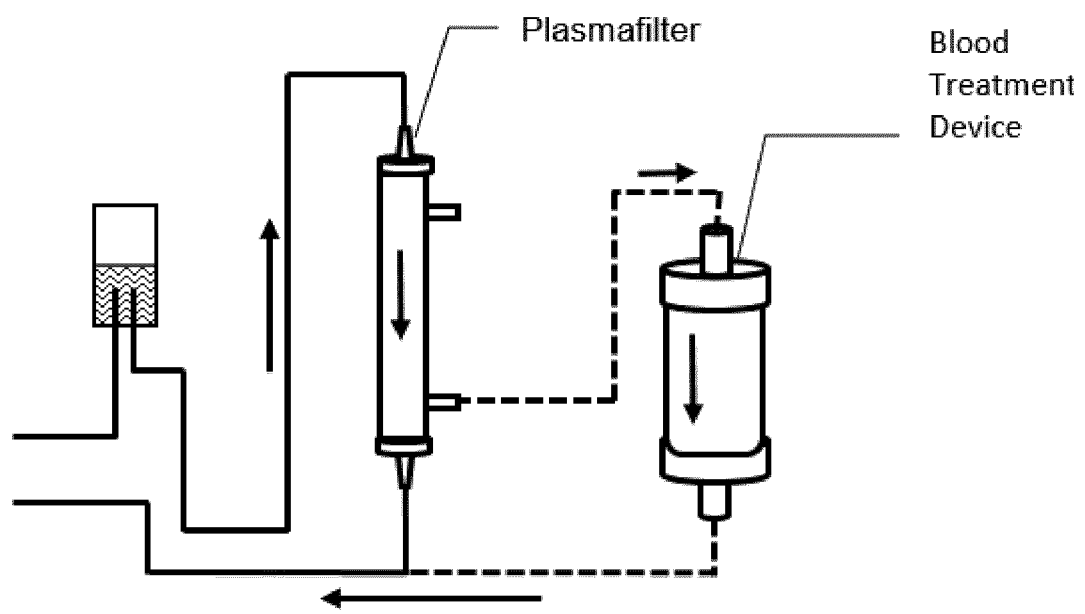

FIG. 5 shows a schematic representation of an extracorporeal treatment circuit comprising a blood treatment device. The device is perfused with blood plasma. In the embodiment shown, a plasma separation filter is used to separate blood plasma from whole blood. The plasma filter generates a plasma fraction comprising the target protein by means of pore sizes ranging from 0.03 µm and 2 µm. The plasma is perfused through the blood treatment device which comprises a matrix based on a non-woven, resin or membrane support to which a ligand having an affinity to a target protein has been bound.

Figure 6:
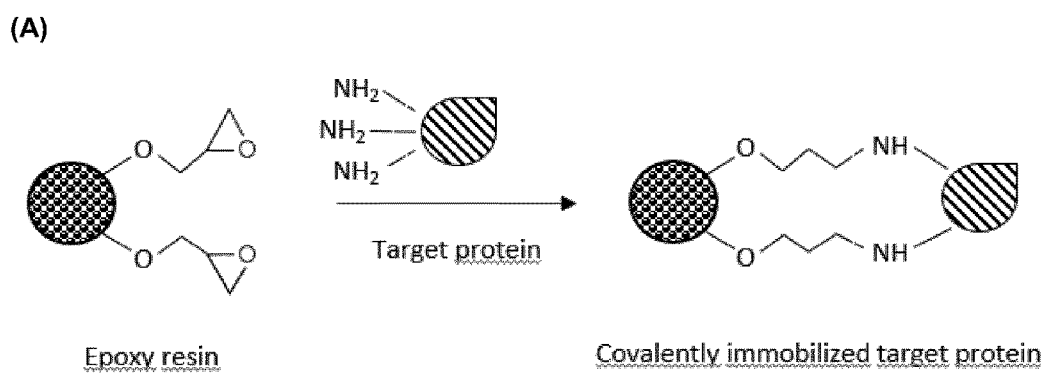
Figure 6:
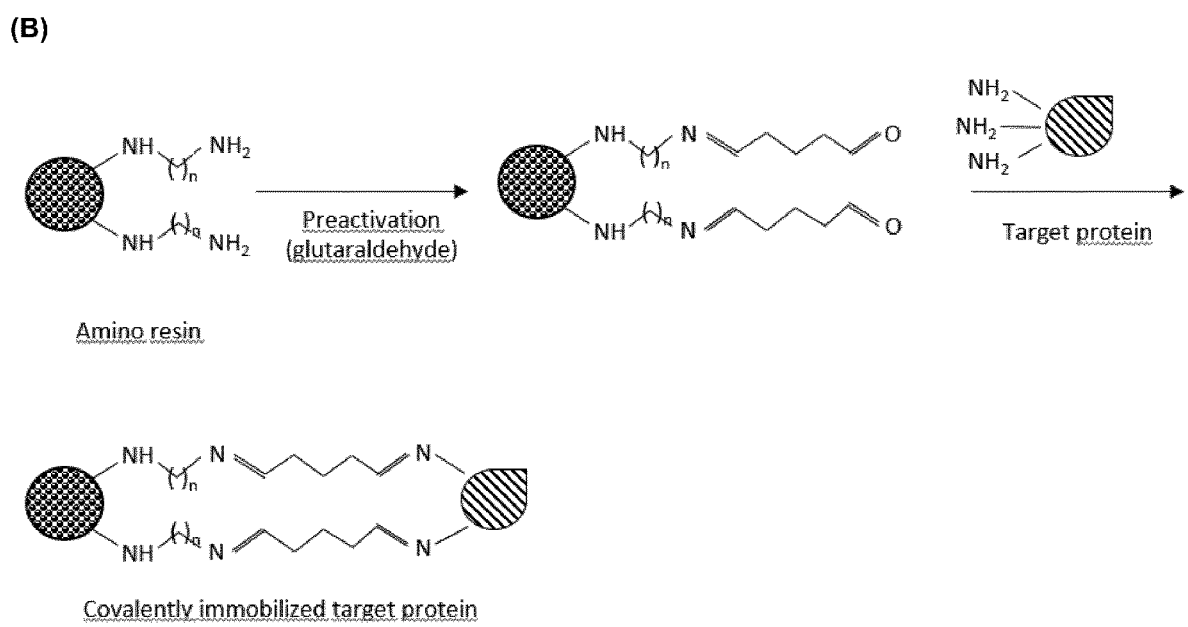

FIGS. 6A-6B show a schematic representation of the covalent coupling of a target protein to an epoxy-activated or an amino support. The support can be a resin, a membrane, including hollow fiber membranes, flat sheet membranes or fiber mats, or a non-woven. Specifically, FIG. 6A shows the direct coupling of the protein via amino groups of the protein to the support (Example 6). FIG. 6B shows the covalent immobilization of enzymes is based on the use of amino resins. Amino resins can be pre-activated with glutaraldehyde and then used in for covalent immobilization of enzymes. Reaction of an aldehyde group with an amino group of the target proteins is fast and forms a Schiff base (imine), resulting in a stable multipoint covalent binding between enzyme and carrier. The imine double bonds can be further reduced with borohydrides.

SUMMARY OF THE INVENTION

In light of the prior art, the technical problem underlying the present invention is to provide alternative and/or improved means for the treatment of ANCA-associated medical conditions. One objective of the invention is therefore the provision of means for reducing, preferably removing PR3 ANCA autoantibodies from patients in need thereof. The present invention seeks to provide such means while avoiding the disadvantages known in the prior art.

The problem is solved by the features of the independent claims. Preferred embodiments of the present invention are provided by the dependent claims.

The invention therefore relates to a blood treatment device configured to remove anti-neutrophil cytoplasmic antibodies (ANCAs) from the blood or blood plasma of a person in need thereof in an extracorporeal blood circuit, wherein the device comprises a matrix, and wherein said matrix comprises a monomeric form of proteinase 3 (PR3).

In the course of analyzing the known PR3 aggregation properties, the inventor has prepared variants of PR3 that exist primarily as monomers in solution and show substantially reduced aggregation behavior.

In some embodiments, this fundamental change in the properties of PR3 is due to minor changes in the primary sequence of the PR3 protein. In some embodiments, a single amino acid substitution is sufficient to reduce oligomerization. In other embodiments, one or more changes in amino acid sequence from the wild type PR3 protein are envisaged in order to provide a monomeric form of PR3.

In one embodiment, the invention relates to a blood treatment device as described herein, wherein the monomeric form of proteinase 3 (PR3) is soluble and preferentially forms monomers compared to oligomers when present in physiological conditions, for example when the PR3 protein is not bound to or comprised by the matrix of the device, i.e. when the protein is free in a physiological solution. Physiological solutions are known to a skilled person, such as in PBS, or other similar buffers.

In one embodiment, the monomeric form of PR3 refers to a PR3 protein that does not comprise the wild type human PR3 sequence. In some embodiments, the monomeric PR3 protein comprises a mutant PR3 sequence, otherwise termed a PR3 variant, or variant sequence. When said monomeric PR3 is present in the device, i.e. comprised or bound in the matrix (a matrix-immobilized species), the protein is typically not considered soluble, as immobilization to a solid phase renders the PR3 variant no longer soluble.

The monomeric form of PR3 enables easier handling, more reliable recombinant production, reduced difficulties in isolating sufficient PR3 quantities, reduced difficulty in manufacturing the device, more reliable immobilization to the matrix/support and more effective ANCA removal due to the avoidance of aggregates.

In one embodiment, the blood treatment device as described herein comprises a monomeric form of proteinase 3 (PR3) that comprises at least a mutation at Ile221.

In one embodiment, the blood treatment device as described herein comprises a monomeric form of proteinase 3 (PR3) that comprises at least a mutation at Ile221 and/or Trp222.

In one embodiment, the blood treatment device as described herein comprises a monomeric form of proteinase 3 (PR3) that comprises at least mutations at Ile221 and Trp222.

In one embodiment, the blood treatment device as described herein comprises a monomeric form of proteinase 3 (PR3) that comprises the Ile221Ala and/or Trp222Ala mutations.

In some embodiments, the wt human PR3 sequence of SEQ ID NO 1 is used as a reference sequence for the amino acid sequence changes mentioned herein, in obtaining PR3 monomeric variants.

A skilled person would not have expected that such minor changes in primary amino acid sequence would lead to the combined beneficial properties of preferential monomer formation compared to wt PR3 protein, thereby leading to improved solubility and ease of handling, combined with maintenance of a suitable structure to present epitopes to anti-PR3 autoantibodies of clinical relevance, and furthermore showing the maintenance of these properties when immobilized in the matrix of a device as described herein. This combination of beneficial properties enables the until now unsuggested approach of using monomeric PR3 protein, preferably modified PR3 amino acid sequences, in an apheresis or blood filtering procedure according to the present invention.

Although the amino acid sequence changes produce significant effects on PR3 solubility they do not otherwise alter the wildtype properties of the enzyme that have been measured.

In some embodiments, the variants are proteolytically active (and therefore properly folded), interact with the only confirmed binding partner of PR3, the neutrophil receptor CD177 and are recognized as effectively by multiple anti-PR3 monoclonal antibodies (FIG. 2) as the wildtype PR3 molecule. These properties enable the employment of essentially monomeric PR3 as described herein in a blood treatment device configured to remove anti-neutrophil cytoplasmic antibodies (ANCAs) from the blood or blood plasma of a person, preferably using an extracorporeal blood circuit. A skilled person would not have expected that disrupting aggregation via mutation would still enable correct epitope formation for clinically relevant ANCA whilst said modified proteins were immobilized. The present invention therefore represents a surprising success based on a combination of beneficial properties.

The PR3 variants described herein are therefore improved reagents for the preparation of a selective PR3-ANCA removal device, or "filter", that can be used in conjunction with plasmapheresis treatment to remove pathogenic PR3-ANCAs from patient blood, serum or plasma.

In some embodiments, the variant or variants can be covalently linked to e.g. an inert solid support housed in a cartridge that can be inserted inline in a plasmapheresis or dialysis assembly. In some embodiments, after the standard separation of blood cells from plasma, the plasma can be passed over this ANCA adsorbing matrix where the variants can specifically capture the circulating PR3-ANCAs from the plasma, which can then be reinfused.

Such a procedure not only has the benefit of targeted removal of only the pathogenic species—thereby leaving the humoral immunity intact—but since the patient's own plasma is reinfused, this improvement of the procedure comes with no additional risk of allergic reaction or infection. In some embodiments, the matrix is prepared by linking the PR3 variant(s) (both fully processed and folded and/or non-processed, partially folded) in multiple orientations in order to allow that multiple possible ANCA epitopes are accessible and, thereby, that the matrix can specifically remove a large proportion of possible PR3-ANCAs from the plasma of a given patient.

In one embodiment, the blood treatment device as described herein comprises a monomeric form of proteinase 3 (PR3) that comprises a mutation that reduces or abolishes protease activity.

In some embodiments, monomeric form of proteinase 3 (PR3) that comprises a mutation that is selected from one or more mutations at His71, Asp118 and/or Ser203, more preferably His71Glu, Asp118Ala and/or Ser203Ala.

In these embodiments, the variant incorporates a further mutation(s) that replaces the catalytic serine, e.g. for alanine (S203A), in order to eliminate the proteolytic activity of the enzyme, thereby also eliminating any possibility of processing of serum proteins during passage over the matrix. In some embodiments, this mutation does not affect the proper folding of the protein or its recognition by ANCAs.

In some embodiments, the invention therefore relates to PR3 proteins with one or more of the following changes in amino acid sequence and their employment in blood treatment devices, i.e. changes at positions:

Ile221, Ile221+Trp222, Ile221+one or more changes at His71, Asp118 and/or Ser203, or Ile221+Trp222+one or more changes at His71, Asp118 and/or Ser203.

In the above embodiments any amino acid change at the given position is envisaged that leads to the properties described herein, i.e. preferably an essentially monomeric form of PR3, with improved solubility in physiological conditions, compared to the wild type human PR3, without significant detrimental effects on PR3-ANCA autoantibody binding. PR3 sequences of the invention may comprise one or more additional amino acid sequence changes if the above properties are evident.

In some embodiments, the invention therefore relates to PR3 proteins with one or more of the following changes in amino acid sequence and their employment in blood treatment devices, i.e. the particular changes:

Ile221Ala, Ile221Ala+Trp222Ala, Ile221Ala+one or more of His71Glu, Asp118Ala and/or Ser203Ala, or Ile221Ala+Trp222Ala+one or more of His71Glu, Asp118Ala and/or Ser203Ala.

In some embodiments of the invention, lysine residues of PR3 sequence (K115, K195 and/or K253) may be maintained as in the WT PR3 sequence, or modified, in order to modify binding properties to the matrix. Lysine residue modification will depend on the linkage chemistry used to immobilize the monomeric PR3 to the matrix, i.e. the solid support. Details on linking modes and chemistries are described in more detail below.

In some embodiments, when amine chemistry (essentially any chemistry exploiting amine linkages) is used, then lysines function as linkage points to the matrix/support. In some embodiments, one or more lysine residues may be modified to prevent immobilization over the modified lysines, thereby directing linkage properties of the molecule.

In some embodiments, there is no difference in the behavior of the three lysines concerning immobilization (i.e. no specific lysine is preferred and therefore the PR3 variants linked in this way are immobilized in all possible orientations allowed by the three lysine locations on the molecule surface). In these embodiments, all possible epitopes would be available for ANCAs in the final matrix.

However, considering that two of the lysines are located close together on the same face of the molecule, in some embodiments immobilization is not uniform, when considering the whole collection of molecules on the matrix.

In other embodiments, one or more lysine residues are mutated (K115, K195 and/or K253 changed over the wt PR3 sequence), preferably to Arginine, thereby maintaining the positive charge and thereby not substantially altering the properties of any possible epitopes that include this residue.

In one embodiment, the blood treatment device as described herein comprises a monomeric form of proteinase 3 (PR3) that comprises one or more changes at K115, K195 and/or K253, preferably K115R, K195R and/or K253R.

In some embodiments, PR3 sequences of the invention may comprise one or more additional amino acid sequence changes if the above properties are evident, i.e. preferably an essentially monomeric form of PR3, with improved solubility in physiological conditions, compared to the wild type human PR3, without significant detrimental effects on PR3-ANCA autoantibody binding.

In embodiments of the invention, the PR3 protein comprises or consists of a variation in the amino acid sequence according to SEQ ID NO. 1 (see below) that exhibits monomeric properties.

In preferred embodiments, the monomeric PR3 protein is SEQ ID NO 1, in which the particular amino acid changes mentioned herein (e.g. Ile221Ala, Ile221Ala+Trp222Ala, Ile221Ala+one or more of His71Glu, Asp118Ala and/or Ser203Ala, Ile221Ala+Trp222Ala+one or more of His71Glu, Asp118Ala and/or Ser203Ala) have been carried out.

In some embodiments, preferred sequences of monomeric PR3 relate to SEQ ID NO 2, 3, 4, 5, 6 or 7.

In some embodiments the PR3-similar sequences employed are functionally equivalent to these PR3 sequences, in other words, such functional equivalence is defined by the ability to bind ANCA and exhibit monomeric properties.

Variation in length of the amino acid sequences as described herein is also encompassed by the present invention. A skilled person is capable of providing amino acid sequence variants that are longer or shorter than SEQ ID NO 2, 3, 4, 5, 6 or 7, which will still exhibit sufficient similarity to the monomeric PR3 variant described herein in order to provide the outcomes desired. For example, shorter variants of SEQ ID NO 2, 3, 4, 5, 6 or 7 comprising 10, 20, 30, 40, 50 or up to 100 amino acids less than the full-length form may also enable effective ANCA binding, as described herein. Fragments of PR3 are therefore also considered. Additionally, longer variants of SEQ ID NO 2, 3, 4, 5, 6 or 7 comprising 10, 20, 30, 40, 50 or up to 100 amino acids any given additional sequence more than the natural PR3 sequence may also enable effective outcomes, as described herein.

In other embodiments of the invention, the PR3 protein employed may comprise or consist of an amino acid sequence with at least 50%, 60%, 70%, 80%, 90% or 95% sequence identity to SEQ ID NO 2, 3, 4, 5, 6 or 7. Preferably the sequence variant comprises at least 80%, 90%, 91, 92, 93, 94, 95, 96, 97, 98 or 99% sequence identity to SEQ ID NO 2, 3, 4, 5, 6 or 7 and preferably exhibits functional analogy to the monomeric PR3 proteins described herein. In preferred embodiments the monomeric PR3 protein employed comprises least 80%, 90%, 91, 92, 93, 94, 95, 96, 97, 98 or 99% sequence identity to SEQ ID NO 2, 3, 4, 5, 6 or 7 and comprises at least one amino acid difference over SEQ ID NO 1, preferably by one or more amino acid substitutions at Ile221, Ile221+Trp222, Ile221+optionally one or more substitutions at His71, Asp118 and/or Ser203, or Ile221+Trp222+optionally one or more substitutions at His71, Asp118 and/or Ser203, and optionally one or more changes at K115, K195 and/or K253, preferably K1 15R, K1 95R and/or K253R.

It is an object of the present invention to provide a blood treatment device adapted to remove at least one PR3-binding ANCA from the blood or blood plasma or other blood-derived sample of a patient who suffers from an ANCA-related disease. In some embodiments, the device is configured to extracorporeally remove said ANCA from the blood or blood plasma of a patient by immobilizing them on a matrix which is contacted with the said blood or blood plasma of the patient and wherein the matrix comprises a support and a monomeric PR3. In some embodiments, the support can consist of a membrane, a resin or a non-woven and the monomeric PR3 has a high binding affinity towards the ANCA described herein. The monomeric PR3 can, for example, be immobilized on the support covalently, through ionic interaction or complexation.

In one embodiment, the blood treatment device as described herein is characterized in that the matrix comprises a support to which the monomeric form of proteinase 3 (PR3) is bound, wherein the support comprises or consists of a material selected from the group consisting of hollow fiber membrane, flat sheet membrane, fiber mat, resin, non-woven and open porous foams, such as polyurethane (PU) foam.

In one embodiment, the blood treatment device as described herein is characterized in that the support is a resin, and the resin is composed of at least one polymer selected from the group consisting of alginate, chitosan, chitin, collagen, carrageenan, gelatin, cellulose, starch, pectin and sepharose; inorganic materials selected from the group consisting of zeolites, ceramics, celite, silica, glass, activated carbon and charcoal; or synthetic polymers, examples of which are provided below.

In one embodiment, the blood treatment device as described herein is characterized in that the support is a resin, and the resin is composed of at least one synthetic polymer, examples of which are provided below.

In one embodiment, the blood treatment device as described herein is characterized in that the support is a hollow fiber membrane, fiber mat or flat sheet membrane, which is composed of at least one polysaccharide derivative or synthetic polymer, examples of which are provided below.

In one embodiment, the blood treatment device as described herein is characterized in that the support is a non-woven and the non-woven is composed of at least one biopolymer selected from the group consisting of polysaccharide, polylactic acid (PLA), polycaprolactone (PCL) and proteins, or of at least one inorganic material selected from the group consisting of $TiO_2$, $SiO_2$ or $Al_2O_3$, or from at least one synthetic polymer, examples of which are provided below.

In one embodiment, the blood treatment device as described herein is characterized in that the blood treatment device is an adsorption cartridge and is perfused with whole blood.

The device can therefore be or comprise an adsorption cartridge comprising a matrix selected from a resin or non-woven material, either of which is functionalized with PR3 configured for binding or immobilizing an ANCA of interest (also referred to as a target protein). Such a device can be a member of an extracorporeal circuit for blood treatment, configured to provide hemodialysis, hemodiafiltration, hemofiltration or plasmapheresis. The device can be the sole blood treatment device within the blood circuit or can be located, for example, upstream or downstream of the dialyzer in a hemodialysis, hemodiafiltration or hemofiltration circuit or can alternatively be immediately connected to the dialyzer at the blood inlet or outlet, wherein the device is configured to be perfused with whole blood. The device can also be a member of an extracorporeal plasmapheresis circuit, wherein the device is perfused with blood plasma or components thereof. The device can also be used in therapeutic plasma exchange (TPE) treatment, wherein the plasma is removed from the patient and is then replaced with a substitute, e.g. fresh frozen plasma. According to one aspect of the invention, the device is used to remove a target protein, such as PR3-ANCA, from the substitute plasma of a donor before or during its administration to the patient.

The device can also be a hybrid filter device which combines hollow fiber membranes and a matrix in the filtrate space of the filter (WO 2014/079680 A1), wherein said matrix consists of a resin which is functionalized with a ligand for binding or immobilizing and thus removing a target ANCA. Such filter can be a member of an extracorporeal circuit configured for performing hemodialysis, hemodiafiltration or hemofiltration, wherein the said filter is located either upstream or downstream of the dialyzer for hemodialysis, hemodiafiltration or hemofiltration, or it can be used as a sole filter device within the said circuit in the absence of such dialyzer. Such device can be used with whole blood.

In one embodiment, the blood treatment device as described herein is characterized in that the blood treatment device is located in an extracorporeal blood circuit through which the blood of the patient passes, and which comprises means for transporting blood from the patient's vascular system to the blood treatment device at a defined flow rate and for returning the treated blood back to the patient.

The device can generally be designed as a hollow fiber membrane filter or dialyzer wherein the membrane constitutes the support to which PR3 is bound on the lumen side of the hollow fibers which is in contact with blood. The membrane can be a hemodialysis membrane for the treatment of renal failure which is additionally functionalized with said PR3 on its lumen side or a plasma separation membrane which is also additionally functionalized with PR3 on its lumen side or, alternatively on the outer side of the hollow fibers and/or its pores.

It is one object of the present invention to provide a hemodialyzer for the purification of blood which can be used for simultaneously treating a patient suffering from renal failure and a disease associated with ANCA. According to one aspect, the lumen side of the hollow fibers of the hemodialyzer are functionalized with PR3.

In one embodiment, wherein the membranes have a pore size which allows for the passage of ANCA, e.g., a plasma separation membrane, the outer surface and/or the pores of the hollow fiber membrane are functionalized with PR3. Alternatively, the lumen side of the plasma separation hollow fiber membranes is functionalized with PR3.

In one embodiment, the device can be a hemodialysis filter for the treatment of renal failure wherein the filter further comprises, in at least one of the end caps, a resin, e.g. in sponge form, or a non-woven, which is functionalized with PR3 for immobilizing said ANCA of interest.

In one embodiment, the blood treatment device as described herein is characterized in that the extracorporeal blood circuit in which the blood treatment device is located further comprises a hemodialyzer which is located upstream or downstream of the blood treatment device.

In one embodiment, the blood treatment device as described herein is characterized in that the extracorporeal blood circuit in which the blood treatment device is located further comprises a plasma dialyzer or centrifuge-based plasma separation system which allows for the separation of a plasma fraction from the blood, and wherein the blood treatment device is located downstream of the plasma outlet port of the plasma dialyzer.

In a further aspect, the invention relates to an extracorporeal blood circuit comprising a blood treatment device as described herein, wherein the extracorporeal blood circuit comprises means for transporting blood or blood plasma from the patient's vascular system to the blood treatment device at a defined flow rate and means for returning the treated blood or blood plasma back to the patient.

In one embodiment, the extracorporeal blood circuit further comprises a hemodialyzer for the hemodialysis of blood, wherein the hemodialyzer is located upstream or downstream of the blood treatment device.

In one embodiment, the extracorporeal blood circuit as described herein is characterized in that the blood treatment device is a hemodialyzer for the hemodialysis of blood, and wherein the hemodialyzer comprises a monomeric form of proteinase 3 (PR3) and is configured to immobilize anti-neutrophil cytoplasmic antibodies (ANCAs).

In one embodiment, the extracorporeal blood circuit further comprises a plasma dialyzer or centrifuge-based plasma separation system configured to separate blood plasma from blood, wherein the blood plasma is passed through the blood treatment device, wherein the blood treatment device is located downstream of the plasma outlet port of the plasma dialyzer.

In one embodiment, the extracorporeal blood circuit as described herein is characterized in the blood treatment device is a plasma dialyzer configured to separate blood plasma from blood, and wherein the plasma dialyzer comprises a monomeric form of proteinase 3 (PR3) and is configured to immobilize anti-neutrophil cytoplasmic antibodies (ANCAs).

In a further aspect, the invention relates to the blood treatment device as described herein for use as a medicament in the treatment of a medical condition associated with anti-neutrophil cytoplasmic antibodies (ANCA). The invention therefore further relates to methods of treating medical conditions associated with anti-neutrophil cytoplasmic antibodies (ANCA) using the devices described herein. According to one aspect, the present invention provides a method of treating or ameliorating at least one symptom of such a disorder.

It is therefore a further object of the present invention to provide a method of treating or ameliorating at least one symptom of an ANCA-related disorder in a patient, wherein the method comprises the step of extracorporeally removing at least one ANCA of interest from the patient by passing the blood or the blood plasma of the patient over a matrix which is configured to bind or immobilize the ANCA, thereby removing it from the blood of the patient. Such removal comprises ex vivo methods wherein, for example, donor blood or donor blood plasma is treated for removing such target ANCA before further use, e.g. for blood transfusion.

It is therefore one object of the present invention to provide for devices, extracorporeal circuits and methods of treating or preventing chronic or acute inflammatory diseases with an autoimmune component wherein the devices are placed in an extracorporeal blood treatment circuit and are configured to remove a target autoantibody from the blood of a patient.

In a further embodiment, the medical condition associated with anti-neutrophil cytoplasmic antibodies (ANCAs) to be treated is an autoimmune disease associated with the presence of anti-PR3 autoantibodies, preferably selected from the group consisting of anti-neutrophil cytoplasmic antibody (ANCA) vasculitides, such as granulomatosis with polyangiitis (GPA, formerly known as Wegener's granulomatosis) or microscopic polyangiitis, pauci-immune crescentic glomerulonephritis or eosinophilic granulomatosis with polyangiitis.

In a further embodiment, the medical condition associated with anti-neutrophil cytoplasmic antibodies (ANCAs) to be treated is anti-neutrophil cytoplasmic autoantibody (ANCA)-associated autoimmune vasculitis (AAV).

DETAILED DESCRIPTION OF THE INVENTION

The present invention is based on the insight that monomeric forms of PR3 may be used to extracorporeally remove at least one ANCA from a patient in need thereof.

All cited documents of the patent and non-patent literature are hereby incorporated by reference in their entirety. All terms are to be given their ordinary technical meaning, unless otherwise described herein.

Proteinase 3:

Proteinase 3 (PR3), also known as Myeloblastin, PRTN3, MBN; MBT; NP4; P29; ACPA; AGP7; NP-4; PR-3; CANCA; C-ANCA, or Wegener autoantigen, is a serine protease that degrades elastin, fibronectin, laminin, vitronectin, and collagen types I, Ill, and IV, and processes Interleukin-8 (FEBS Lett 352: 231-235), IL-1beta (JASN 23: 470-482), kinase inhibitor p21waf1 (JBC 277:47338-47347), annexin-1 (JBC 282:29998-30004), protease-activated receptor-1 (Arterioscler Thromb Vasc Biol 33: 275-284) and the C5a receptor (J. Immunol. 192:1787-1795). PR3 is the major autoantigen in anti-neutrophil cytoplasmic autoantibody (ANCA)-associated vasculitis (Wegener's granulomatosis).

The PR3 protein is described as having a length of 256 amino acids and an estimated mass of 27807 Da. The reported wild type human PR3 sequence is recorded in public sequence databases, for example under UniProtKB-P24158 (PRTN3_HUMAN):

```
Wt human PR3 (SEQ ID NO 1):
MAHRPPSPALASVLLALLLSGAARAAEIVGGHEAQPHSRPYMASLQMRG

NPGSHFCGGTLIHPSFVLTAAHCLRDIPQRLVNVVLGAHNVRTQEPTQQ

HFSVAQVFLNNYDAENKLNDVLLIQLSSPANLSASVATVQLPQQDQPVP

HGTQCLAMGWGRVGAHDPPAQVLQELNVTVVTFFCRPHNICTFVPRRKA

GICFGDSGGPLICDGIIQGIDSFVIWGCATRLFPDFFTRVALYVDWIRS

TLRRVEAKGRP
```

In some embodiments, the wt human PR3 sequence of SEQ ID NO 1 is used as a reference sequence for the amino acid sequence changes mentioned herein, in obtaining PR3 monomeric variants. Further preferred sequences relate to:

```
Ile221X (SEQ ID NO 2):
MAHRPPSPALASVLLALLLSGAARAAEIVGGHEAQPHSRPYMASLQMRG

NPGSHFCGGTLIHPSFVLTAAHCLRDIPQRLVNVVLGAHNVRTQEPTQQ

HFSVAQVFLNNYDAENKLNDVLLIQLSSPANLSASVATVQLPQQDQPVP

HGTQCLAMGWGRVGAHDPPAQVLQELNVTVVTFFCRPHNICTFVPRRKA

GICFGDSGGPLICDGIIQGIDSFVXWGCATRLFPDFFTRVALYVDWIRS

TLRRVEAKGRP
``` wherein X is any amino acid other than lie, preferably is Ala, Pro, Gly, Glu, Asp, Gln, Asn, Ser, Thr, more preferably is Ala.

```
Ile221X + Trp222Z (SEQ ID NO 3):
MAHRPPSPALASVLLALLLSGAARAAEIVGGHEAQPHSRPYMASLQMRG

NPGSHFCGGTLIHPSFVLTAAHCLRDIPQRLVNVVLGAHNVRTQEPTQQ

HFSVAQVFLNNYDAENKLNDVLLIQLSSPANLSASVATVQLPQQDQPVP

HGTQCLAMGWGRVGAHDPPAQVLQELNVTVVTFFCRPHNICTFVPRRKA

GICFGDSGGPLICDGIIQGIDSFVXZGCATRLFPDFFTRVALYVDWIRS

TLRRVEAKGRP
``` wherein X is any amino acid other than lie, preferably is Ala, Pro, Gly, Glu, Asp, Gln, Asn, Ser, Thr, more preferably is Ala, and wherein Z is any amino acid other than Trp, preferably is Ala, Pro, Gly, Glu, Asp, Gin, Asn, Ser, Thr, more preferably is Ala.

Ile221X + one or more changes at His71, Asp118 and/or Ser203 (SEQ ID NO 4):
MAHRPPSPALASVLLALLLSGAARAAEIVGGHEAQPHSRPYMASLQMRG

NPGSHFCGGTLIHPSFVLTAAU1CLRDIPQRLVNVVLGAHNVRTQEPTQ

QHFSVAQVFLNNYDAENKLNU2VLLIQLSSPANLSASVATVQLPQQDQP

VPHGTQCLAMGWGRVGAHDPPAQVLQELNVTVVTFFCRPHNICTFVPRR

KAGICFGDU3GGPLICDGIIQGIDSFVXWGCATRLFPDFFTRVALYVDW

IRSTLRRVEAKGRP wherein X is any amino acid other than Ile, preferably is Ala, Pro, Gly, Glu, Asp, Gln, Asn, Ser, Thr, more preferably is Ala, and wherein U1 is any amino acid other than His, preferably is Ala, Pro, Gly, Glu, Asp, Gln, Asn, Ser, Thr, more preferably is Glu, and/or wherein U2 is any amino acid other than Asp, preferably is Ala, Pro, Gly, Glu, Gln, Asn, Ser, Thr, more preferably is Ala, and/or wherein U3 is any amino acid other than Ser, preferably is Ala, Pro, Gly, Glu, Asp, Gln, Asn, Thr, more preferably is Ala.

Ile221X + Trp222Z + one or more changes at His71, Asp118 and/or Ser203 (SEQ ID NO 5):
MAHRPPSPALASVLLALLLSGAARAAEIVGGHEAQPHSRPYMASLQMRG

NPGSHFCGGTLIHPSFVLTAAU1CLRDIPQRLVNVVLGAHNVRTQEPTQ

QHFSVAQVFLNNYDAENKLNU2VLLIQLSSPANLSASVATVQLPQQDQP

VPHGTQCLAMGWGRVGAHDPPAQVLQELNVTVVTFFCRPHNICTFVPRR

KAGICFGDU3GGPLICDGIIQGIDSFVXZGCATRLFPDFFTRVALYVDW

IRSTLRRVEAKGRP wherein X is any amino acid other than Ile, preferably is Ala, Pro, Gly, Glu, Asp, Gln, Asn, Ser, Thr, more preferably is Ala, and wherein Z is any amino acid other than Trp, preferably is Ala, Pro, Gly, Glu, Asp, Gln, Asn, Ser, Thr, more preferably is Ala, and wherein U1 is any amino acid other than His, preferably is Ala, Pro, Gly, Glu, Asp, Gln, Asn, Ser, Thr, more preferably is Glu, and/or wherein U2 is any amino acid other than Asp, preferably is Ala, Pro, Gly, Glu, Gln, Asn, Ser, Thr, more preferably is Ala, and/or wherein U3 is any amino acid other than Ser, preferably is Ala, Pro, Gly, Glu, Asp, Gln, Asn, Thr, more preferably is Ala.

Ile221Ala + Ser203Ala (SEQ ID NO 6):
MAHRPPSPALASVLLALLLSGAARAAEIVGGHEAQPHSRPYMASLQMRG

NPGSHFCGGTLIHPSFVLTAAHCLRDIPQRLVNVVLGAHNVRTQEPTQQ

HFSVAQVFLNNYDAENKLNDVLLIQLSSPANLSASVATVQLPQQDQPVP

HGTQCLAMGWGRVGAHDPPAQVLQELNVTVVTFFCRPHNICTFVPRRKA

GICFGDAGGPLICDGIIQGIDSFVAWGCATRLFPDFFTRVALYVDWIRS

TLRRVEAKGRP

Ile221Ala + Trp222Ala + Ser203Ala (SEQ ID NO 7):
MAHRPPSPALASVLLALLLSGAARAAEIVGGHEAQPHSRPYMASLQMRG

NPGSHFCGGTLIHPSFVLTAAHCLRDIPQRLVNVVLGAHNVRTQEPTQQ

HFSVAQVFLNNYDAENKLNDVLLIQLSSPANLSASVATVQLPQQDQPVP

HGTQCLAMGWGRVGAHDPPAQVLQELNVTVVTFFCRPHNICTFVPRRKA

GICFGDAGGPLICDGIIQGIDSFVAAGCATRLFPDFFTRVALYVDWIRS

TLRRVEAKGRP

The PR3 protein is known to be processed, producing a signal peptide (aa 1-25), a propeptide (aa 26-27), a chain peptide (aa 28-248) and a propeptide (aa 249-256).

The various functionally equivalent fragments are therefore encompassed in the invention. Removing signal peptides and/or propeptides may result in functional monomeric PR3 variants.

The PR3 protein appears to be highly conserved in Rhesus monkey, cow, mouse, rat, mosquito, and frog, the PR3 sequences of which are hereby incorporated by reference.

Alternative recombinant PR3 variants have also been described previously, such as in the description of the crystal structure of PR3, as described in Fujinaga et al (J Mol Biol. 1996 Aug. 16; 261(2):267-78). Numbering of amino acids may also differ in the prior art, for example as in Fujinaga et al (J Mol Biol. 1996 Aug. 16; 261(2):267-78) and in Jerke et al (2017, Scientific Reports 7:43328). A skilled person is capable of determining sequence numbering and correct reference sequences as is required based on appropriate databases, such as NCBI and UniProtKB.

In some embodiments, a PR3 protein with substantially the same or a similar amino acid sequence to SEQ ID NO 2, 3, 4, 5, 6, or 7, or fragments thereof, and comprising amino acid sequence changes leading to monomeric properties, may be employed. Examples are fragments of PR3, such as naturally occurring PR3 fragments, homologues or derivatives with essentially the same properties or functional analogy to the examples of monomeric PR3 as described herein.

As used herein, the term "substantially the same or similar amino acid sequence" includes an amino acid sequence that is similar, but not identical, to the reference amino acid sequence. For example, an amino acid sequence, i.e., polypeptide, that has substantially the same amino acid sequence as PR3 in SEQ ID NO 2, 3, 4, 5, 6, or 7, and comprises one or more modifications, such as amino acid additions, deletions, or substitutions relative to the amino acid sequence of SEQ ID NO 2, 3, 4, 5, 6, or 7, may be employed, provided that the modified polypeptide retains substantially at least one biological activity of PR3 such as those described above, i.e. a preferentially monomeric form of PR3, with improved solubility in physiological conditions compared to the wild type human PR3, without significant detrimental effects in PR3-ANCA autoantibody binding compared to wtPR3.

A particularly useful modification of a polypeptide of the present invention, or a fragment thereof, is a modification that confers, for example, increased stability or reactivity. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The amino acid sequences may also comprise 0 to 100, 2 to 50, 5 to 20, or for example 8 to 15, or any value from 0 to 20, amino acid additions or deletions at either the N- and/or C-terminus of the proteins. The termini may also be modified with additional linker sequences, or removal of sequences, as long as the autoantibody binding properties and immunoreactivity of the protein is essentially maintained and the ANCA autoantibodies as described herein bind in an analogous manner to the PR3 sequence provided, in addition to preferably an essentially or preferentially monomeric form of PR3, with improved solubility in physiological conditions, compared to the wild type human PR3.

Various ways of preparing functionally analogous peptides have been disclosed in the prior art. Peptides designed starting from the peptides of the invention using such methods are included in the teaching according to the invention. For example, one way of generating functionally analogous peptides has been described in PNAS USA 1998, Oct. 13, 95(21), 12179-84; WO 02/38592; the above teachings are hereby incorporated in the disclosure of the invention. That is, all peptides, peptide fragments or structures comprising peptides generated using the methods mentioned above—starting from the peptides of the invention—are peptides according to the invention, provided they accomplish the object of the invention and, in particular, interact with the pathogenic autoantibodies and show improved monomeric properties over wtPR3.

As used herein, the term "monomeric form of proteinase 3 (PR3)" relates to any PR3 protein that forms monomers in physiological solution to a greater extent than wild type PR3.

In some passages of the specification, the term "PR3" is used without explicit reference to "monomeric PR3". A skilled person is capable of deducing whether wtPR3 or monomeric PR3 variants are intended.

Preferred conditions for assessing monomer properties are in an experimental setting in a buffer of 20 mM HEPES, 150 mM NaCl buffer, at pH 7.5. Alternatively, a buffer comprising 20 mM HEPES, 150 mM NaCl, 0.02% laurylmaltoside, pH 7.4 may be employed to assess monomer properties. Alternatively, a plasma, blood or serum condition could be used. Whether a PR3 forms monomers to a greater or lesser extent than wild type PR3 can be assessed using techniques established in the art, for example size exclusion chromatography as described below in the examples. Other techniques for assessing the monomeric properties of PR3 relate to dynamic light scattering combined with Gel Filtration, native gel electrophoresis, small angle X-ray scattering (SAXS) and/or mass spectrometry based on techniques known to a skilled person.

The monomeric PR3 of the invention is preferentially monomeric compared to oligomeric when in solution. This property differs from wild-type PR3 protein, which preferentially forms aggregates or oligomers when present in physiological conditions. References to a monomeric form of PR3 therefore refer to the property of the molecule itself when in physiological conditions. In some embodiments, the monomericity or solubility of the monomeric PR3 form when comprised by the matrix (preferably immobilized to the matrix) may differ compared to when the monomeric form of PR3 is present free in solution.

In some embodiments, the sequence of PR3 employed is a mutated, or not a naturally occurring sequence, for example a sequence not according to SEQ ID NO 1.

In the context of the device of the present invention, the monomer PR3 protein is in one embodiment covalently (i.e. irreversibly) attached to the matrix. Monomer PR3 variants covalently attached to a matrix are not known to aggregate and do maintain their monomeric properties. Other forms of immobilizing PR3 also have no detrimental impact on the monomeric properties of PR3. The PR3 variants described herein therefore also exhibit monomeric properties (form monomers in physiological solution to a greater extent than wild type PR3) and ANCA binding properties in physiological conditions, either in buffer solutions described or while present immobilized and surrounded in blood, serum or plasma, when immobilized to a matrix in the device of the invention.

Diseases to be Treated:

The term "autoimmune disease" as used herein refers to any given disease associated with and/or caused by the presence of autoantibodies. Autoimmune diseases arise from an abnormal immune response of the body against substances and tissues normally present in the body (autoimmunity). This may be restricted to certain organs or involve a particular tissue.

The term "medical condition associated with anti-neutrophil cytoplasmic antibodies (ANCA)" as used herein refers to any medical condition in which ANCA have been detected, preferably those with an established pathological contribution to disease.

ANCAs are associated with small vessel vasculitides, including granulomatosis with polyangiitis, microscopic polyangiitis, primary pauci-immune necrotizing crescentic glomerulonephritis (a type of renal-limited microscopic polyangiitis), eosinophilic granulomatosis with polyangiitis (previously known as Churg-Strauss syndrome) and drug induced vasculitides.

PR3 directed c-ANCA is present in 80-90% of granulomatosis with polyangiitis, 20-40% of microscopic polyangiitis, 20-40% of pauci-immune crescentic glomerulonephritis and 35% of eosinophilic granulomatosis with polyangiitis. c-ANCA (atypical, a kind of PR3 ANCA) is present in 80% of cystic fibrosis (with BPI as the target antigen) and also in inflammatory bowel disease, primary sclerosing cholangitis and rheumatoid arthritis (with antibodies to multiple antigenic targets). Atypical ANCA is associated with drug-induced systemic vasculitis, inflammatory bowel disease and rheumatoid arthritis (Savige, J et al (2000) Antineutrophil cytoplasmic antibodies and associated diseases: a review of the clinical and laboratory features". Kidney International. 57 (3): 846-62).

The term "anti-neutrophil cytoplasmic antibody (ANCA) vasculitides" as used herein refers to a group of diseases exhibiting PR3 ANCA characterized by destruction and inflammation of small vessels. Examples, without limitation, are granulomatosis with polyangiitis (GPA, formerly known as Wegener's granulomatosis) or microscopic polyangiitis, pauci-immune crescentic glomerulonephritis or eosinophilic granulomatosis with polyangiitis. One example is antineutrophil cytoplasmic autoantibody (ANCA)-associated autoimmune vasculitis (AAV).

According to one embodiment of the invention, patients requiring treatment using the device described herein comprising monomeric PR3 are identified using standard methods, for example by assessing the blood or a sample derived from the blood of a patient for the presence of ANCA that bind PR3.

Methods suitable for diagnosing a disease associated with ANCA include for example ELISA or indirect immunofluorescent tests. Detection of ANCAs is a well-established diagnostic test used to evaluate suspected necrotizing vasculitis of small blood vessels. The diagnostic utility of ANCA testing depends on the type of assay performed and on the clinical setting and can be adjusted to the conditions of the patient. Most laboratories worldwide use standard indirect immunofluorescence tests (IFT) to screen for ANCA and then confirm positive IFT results with antigen-specific tests for proteinase 3 (PR3) and myeloperoxidase (MPO). Developments such as automated image analysis of immunofluorescence patterns, so-called third-generation PR3-ANCA and MPO-ANCA ELISA, and multiplex technology may also be employed (Csernok et al, Nat Rev Rheumatol. 2014 August; 10(8):494-501).

According to one embodiment of the invention, the diagnostic and monitoring methods described herein are used to monitor the subject during therapy or to determine effective therapeutic dosages or to determine the number and frequency of treatments needed.

According to another aspect, the method is provided to patients that additionally show either acute renal impairment or failure or are dependent on chronic renal replacement therapy. Patients with ANCA and who show renal impairment are a target group of patients to be handled.

Anti-Neutrophil Cytoplasmic Antibodies:

As used herein, the term "anti-neutrophil cytoplasmic antibodies (ANCAs)" refer to autoantibodies, primarily but not exclusively of the IgG type, that bind to antigens in the cytoplasm of neutrophil granulocytes (the most common type of white blood cell) and monocytes.

ANCA can be divided into four patterns when visualized by immunofluorescence; cytoplasmic ANCA (c-ANCA), C-ANCA (atypical), perinuclear ANCA (p-ANCA) and atypical ANCA (a-ANCA), also known as x-ANCA. c-ANCA shows cytoplasmic granular fluorescence with central interlobular accentuation. c-ANCA (atypical) shows cytoplasmic staining that is usually uniform and has no interlobular accentuation. p-ANCA has three subtypes, classical p-ANCA, pANCA without nuclear extension and granulocyte specific-antinuclear antibody (GS-ANA). Classical p-ANCA shows perinuclear staining with nuclear extension, p-ANCA without nuclear extension has perinuclear staining without nuclear extension and GS-ANA shows nuclear staining on granulocytes only. a-ANCA often shows combinations of both cytoplasmic and perinuclear staining (Advanced atlas of autoantibody patterns. Birmingham: The Binding Site. ISBN 0704485109).

The so-called c-ANCA antigen is specifically proteinase 3 (PR3). The term "PR3 ANCA" may refer to any autoantibody binding PR3.

p-ANCA antigens include myeloperoxidase (MPO) and bacterial permeability increasing factor (BPI). Classical p-ANCA occurs with antibodies directed to MPO. p-ANCA without nuclear extension occurs with antibodies to BPI, cathepsin G, elastase, lactoferrin and lysozyme. Other less common antigens include HMG1 (p-ANCA pattern), HMG2 (p-ANCA pattern), alpha enolase (p and c-ANCA pattern), catalase (p and c-ANCA pattern), beta glucuronidase (p-ANCA pattern), azurocidin (p and c-ANCA pattern), actin (p and a-ANCA) and h-lamp-2 (c-ANCA)

In some embodiments, the one or more of the proteins MPO, BPI, cathepsin G, elastase, lactoferrin, lysozyme, HMG1, HMG2, alpha enolase, catalase, beta glucuronidase, azurocidin, actin and h-lamp-2 as the antigen of p-ANCA, may be employed in combination with PR3 (simultaneously, in a separate or the same device, or prior to or after PR3 device treatment) in order to remove ANCA in an analogous manner as described herein for PR3. These proteins have been described as antigens of ANCA and their combined use can enhance the removal of more ANCA than via the use of PR3 alone.

Devices:

The invention includes devices which are configured to be located in an extracorporeal blood circuit through which the blood of a patient passes and which comprises means for transporting blood from the patient's vascular system to a blood treatment device at a defined flow rate and then returning the treated blood back to the patient, and wherein the device is further configured to immobilize at least one ANCA, thereby removing it from the blood of the patient.

Extracorporeal devices and methods for removing target components from the blood of a patient have been described before. For example, WO 2013/020967 A1 discloses the use of a device and matrix for the immobilization and removal of blood group antibodies from a patient. U.S. Pat. No. 8,969,322 B2 described an extracorporeal apheresis procedure for the removal of soluble Flt-1 receptor from the blood of a patient by means of a device comprising dextran sulfate.

However, despite a wealth of literature on diseases connected to ANCAs, extracorporeal treatment approaches based on modified PR3 proteins as described herein have to the knowledge of the inventors not so far been described.

Accordingly, in one aspect, the invention discloses devices comprising a matrix which is designed for the specific removal from the blood of a patient in an extracorporeal circuit of at least one target protein (ANCA) which is involved in autoimmune disease. According to another aspect, the invention discloses extracorporeal circuits comprising said devices and describes how such circuits should be configured to effectively treat the blood of the patient in need. According to yet another aspect, the invention provides for a method for reducing the level of at least one target protein (ANCA) in a bodily fluid of a subject, comprising the step of extracorporeally removing the target protein from the patient by passing the blood or the blood plasma of the patient through a device according to the invention. According to one aspect, the device according to the invention comprising an adsorbent, e.g. in the form of beads, has an active surface are, per device, in the range of between 0.5 and 50000 $m^2$ when used in whole blood perfusion (hemoperfusion). According to another aspect, the said device according to the invention has an active surface are, per device, in the range of between 0.5 and 50000 $m^2$ when used in whole plasma perfusion (therapeutic apheresis). According to yet another aspect, the said devices for hemoperfusion and/or whole plasma perfusion have an active surface area, per device, in the range of between 0.5 and 10000 $m^2$.

The expression "blood" as used herein refers to whole blood which contains all components of the blood of an organism, including red cells, white cells, and platelets suspended in plasma. The expression "blood plasma" refers to the fluid, composed of about 92% water, 7% proteins such as albumin, gamma globulin, fibrinogen, complement factors, clotting factors, and 1% mineral salts, sugars, fats, electrolytes, hormones and vitamins which forms part of whole blood but no longer contains red and white cells and platelets. In the context of the present invention, the expression "blood plasma" also refers to specific fractions of the above defined blood plasma in its standard meaning, such as, for example, blood serum.

Various known methods can be used to immobilize a target such as a target protein according to the invention. Such immobilization preferably is specific or selective in that it immobilizes the target protein of interest whereas other proteins and components present in blood or blood plasma or a sample thereof (in vitro) are not immobilized to a significant degree.

According to one embodiment of the invention, one such method is affinity chromatography, also called affinity purification, whereby the target protein ANCA is removed from a solution by virtue of its specific binding properties to an immobilized PR3. Affinity chromatography can be defined as a type of liquid chromatography that uses a biologically related agent, that is, an "affinity ligand" or a "ligand", such as PR3, for selectively retaining a target molecule (ANCA) or to study biological interactions (Hage et al., J. Pharm. Biomed. Anal. (2012), 69, 93-105); Ayyar et al., Methods (2012) 56: 116-129).

"Specific binding" generally refers to a physical association between a target molecule (e.g., ANCA) and a binding molecule such as an antibody or ligand (PR3). The association is typically dependent upon the presence of a particular structural feature of the target such as an antigenic determinant, epitope, binding pocket or cleft, recognized by the binding molecule. The affinity ligand (PR3) is immobilized on a support and together with it forms a matrix. It is then used to selectively bind a given target or group of targets within or from a sample, such as, for example, blood or blood plasma. Because of the selective or highly selective nature of many affinity ligands, the matrix can be used to immobilize, bind, isolate, measure, or study specific targets even when they are present in complex biological samples such as blood or blood plasma. In some embodiments, the affinity (as measured by the equilibrium dissociation constant, $K_d$) of two molecules (e.g. between a ligand and a target protein) that exhibit specific binding, is $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, e.g., between $10^{-13}$ M and $10^{-4}$ M (or within any range having any two of the afore-mentioned values as endpoints) under the conditions tested, e.g., under physiological conditions regarding, for example, salt concentration, pH, and/or temperature, etc., that reasonably approximate corresponding conditions applied during use according to the invention. Binding affinity can be measured using any of a variety of methods known in the art. For example, assays based on isothermal titration calorimetry or surface plasmon resonance (e.g., Biacore® assays) can be used in certain embodiments. According to one embodiment of the invention, the ligand should have an affinity range of from $10^{-6}$ M to $10^{-13}$ M for the target protein.

The expression "matrix" as used herein thus refers to a material which can be used for affinity chromatography of a target protein according to the invention. Such matrix as used in the context of the present invention comprises a support to which a ligand is bound. The support therefore serves as a carrier for the ligand, even though it has to fulfil other functions as well.

The expression "binding" of or "to bind" (to) a ligand to the support for providing a matrix which can be used in a device according to the invention as used herein refers to a non-covalent or covalent interaction that holds two molecules together. According to one embodiment of the invention, the expression refers to a covalent interaction, i.e. to covalently bound ligands. Noncovalent interactions include, but are not limited to, hydrogen bonding, ionic interactions among charged groups, van der Waals interactions, and hydrophobic interactions among nonpolar groups. One or more of these interactions can mediate the binding of two molecules to each other. Binding may otherwise be specific or selective, or unspecific. According to one embodiment of the invention, the expression "binding" of or "to bind" (to) refers to a covalent attachment of the ligand to the support. According to another embodiment of the invention, the expression "binding" of or "to bind" (to) refers to an ionic interaction for the attachment of the ligand to the support.

The expression "ligand" or "ligands" as used herein, generally refers to a molecule which is characterized by its affinity to the target protein. In some embodiments, the monomeric PR3 protein is intended as the ligand, attached to the device, in order to bind the target protein, in this case PR3 binding ANCA.

The ligand is further characterized by its specificity for the target protein. It is characterized, according to one embodiment of the invention, by its immobilization feasibility, stability during its use in methods of treating or ameliorating at least one symptom of an ANCA-related disease, and by the retention of target binding capacity after attachment to the matrix over a prolonged time for storage and duration of a treatment of at least 2 hours, preferably of at least 4, at least 8 or at least 12 hours.

According to another embodiment of the invention, the expression "ligand" or "ligands" represent affinity ligands which are PR3 derived peptides, comprising or consisting pf PR3 sequences or sequence variants, and have been selected based on their binding properties to ANCA.

The term "immunoaffinity chromatography" (IAC) is generally used for an affinity chromatography method in which the matrix comprises an antibody or an antigen binding fragment thereof (Moser et al., Bioanalysis (2010) 2:769-790). In the context of the present invention the matrix comprises an antigen (PR3) which binds an antibody (ANCA target). The selective binding of a target protein to the immobilized antigen is a result of a large variety of noncovalent interactions that can occur between an antibody and an antigen such as the target protein according to the invention and can result in association equilibrium constants in the range of $10^5$-$10^{12}$ M$^{-1}$. Due to the generally large size of naturally occurring antigens, antibodies that bind to several different regions of the antigen with a range of binding affinities are often generated. Each individual location on an antigen/target protein that can bind to an antibody is called an epitope. According to one aspect of the present invention, the antibody target can bind to any epitope presented by the PR3 protein, provided the association equilibrium constants of the interaction are in the range of $10^5$-$10^{15}$ M$^{-1}$. According to another aspect of the invention, the association equilibrium constants of the interaction are in the range of $10^6$-$10^{12}$ M$^{-1}$, are in the range of $10^6$-$10^{10}$ M$^{-1}$, are in the range of $10^8$-$10^{10}$ M$^{-1}$, or are in the range of $10^8$-$10^{12}$ M$^{-1}$.

According to one specific embodiment of the invention, the PR3 reagent or fragments thereof comprise affinity tags for immobilizing them on the support. Affinity tags can be used for purifying the protein during their production and/or for immobilizing them on the support of the matrix of the present invention. Affinity tags can be short polypeptide sequences or whole proteins, co-expressed as fusion partners with the target proteins. Apart from facilitating purification and quick immobilization, fusion tags are sometimes also advantageous in increasing the expression and solubility of recombinant proteins. Affinity tags can be used to ensure proper orientation of the protein, or various orientations can be used, thus, making the functional domains accessible for interaction. They also provide a system for immobilization, quantitation and detection of a target protein and are thus specifically interesting also for analytical purposes, including immunoassays. Different types of affinity tags are well known in the art (Terpe, Appl Microbiol Biotechnol (2003) 60:523-533), wherein polyhistidine or His$_6$-tags are especially well described and are one option for binding ligands according to the invention to the support material. Affinity tags which can otherwise be used for binding the ligand to the support can be selected from the group comprising C-myc-tags, FLAG-tags, and Hemagglutinin (HA)-tags.

According to another embodiment of the invention, PR3 protein can also be immobilized onto supports by using a secondary ligand to adsorb the PR3. This can be accomplished by using PR3 that has been reacted with biotin or biotinylated, and then adsorbed to a support that contains immobilized avidin or streptavidin. One possible biotinylation technique is to incubate PR3 with N-hydroxysuccinimide-D-biotin at pH 9. The noncovalent linkage of biotin to strepavidin or avidin can then be used to immobilize these proteins. These linkages have association equilibrium constants in the range of $10^{13}$-$10^{15}$ M$^{-1}$.

According to another embodiment of the invention, the PR3 proteins are covalently attached to the support as further detailed below and/or as described the prior art (Cuatrecasas, J Biol Chem (1970) 245:3059-3065; Nisnevitch et al., J Biochem Biophys Methods (2001) 49:467-480). Covalent coupling generally includes either covalent non-site directed attachment of the protein which is based on utilizing functional groups on either the support and/or the protein (Nisnevitch et al., J Biochem Biophys Methods (2001) 49:467-480, Section 2.3). According to another embodiment of the invention the covalent attachment of proteins is a site-directed attachment of the protein (Nisnevitch et al., J Biochem Biophys Methods (2001) 49:467-480, Section 2.4; Makaraviciute et al., Biosensors and Bioelectronics (2013) 50:460-471). Essentially, technical guidance for attaching an antibody to a matrix, as is typically carried out in immunoaffinity approaches, may be applied to immobilize PR3 protein on the support, in order to immobilize and remove ANCA from the blood or plasma or a patient. References disclosed herein regarding antibody immobilization to a support or matrix are also considered potentially relevant for immobilizing monomeric PR3 variants.

The expression "support" as used herein refers to the portion of the matrix which serves as the "substrate" or "support material" to which the ligands (PR3) according to the invention are bound. Such support or support material is sometimes also referred to as "adsorption material" or "adsorber" and such expressions shall be encompassed by the expression "support" as used herein. A suitable support according to the present invention should be uniform, hydrophilic, mechanically and chemically stable over the relevant pH range and temperature with no or a negligible leaching of the ligands during use, selective, exhibit minimum non-specific absorption, and should otherwise be blood compatible, i.e. does not induce adverse reactions including the activation of the complement system or other immunological pathways, has good flow characteristics for whole blood and/or blood plasma, and provides a large surface area for ligand attachment.

The support can be a resin, a membrane or a non-woven. The expression "resin" as used herein, refers to an insoluble material which can take the form of translucent gels or gel beads or microporous beads having pores and an opaque appearance, or can take the form of a sponge. Such resins can be natural or bio-polymers, synthetic polymers and inorganic materials. Agarose, dextrose and cellulose beads are commonly employed natural supports. Synthetic polymeric or organic supports are mostly based on acrylamide, polystyrene and polymethacrylate derivatives, whereas, porous silica and glass are some frequently used inorganic supports. Other materials which can be used in accordance with the invention are described below.

According to one embodiment of the invention, the resin is composed of polymers selected from the group consisting of alginate, chitosan, chitin, collagen, carrageenan, gelatin, cellulose, starch, pectin and sepharose; inorganic materials selected from the group consisting of zeolites, ceramics, celite, silica, glass, activated carbon and char-coal; or synthetic polymers selected from the group consisting of polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate (PAA), polymethyl methacrylate (PMMA), polyacrylamide, polyglycidyl methac-rylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), eth-ylene vinyl acetate (EVA), ethylene vinyl alcohol (EVOH), polyamideimide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allylbenzoic acid), poly(glycidyl acrylate), polyglycidyl methacrylate (PGMA), acrylonitrile butadiene styrene (ABS), polydivinylbenzene (PDVB), poly(allyl glycidyl ether), poly(vinyl glycidyl ether), poly(vinyl glycidyl urethane), polyallylamine, pol-yvinylamine, copolymers of said polymers and any of these polymers modified by introduction of functional groups. According to one specific embodiment of the invention, the support is selected from the group consisting of styrene divinylbenzene (DVB) and derivatives, polymethyl methacrylate (PMMA) and derivatives, and polyglycidyl methacrylate (PGMA) and derivatives.

As mentioned above, the ligand according to the invention may be covalently bound to the support. The support which forms the basis for the generation of a matrix wherein said ligand can be attached covalently must provide or facilitate chemical activation, thus allowing the chemical coupling of the ligands. Many coupling methods for immobilizing ligands, such as antibodies or fragments thereof, are well known in the art. In general, the activation chemistry should be stable over a wide range of pH, buffer conditions and temperature resulting in negligible leaching of ligands. The coupling method should avoid improper orientation, multisite attachment or steric hindrance of the ligand, which may cause masking of the binding sites and, subsequently, lead to loss of activity. Site-directed attachment and/or spacers can be considered for immobilizing the ligand onto the support. The ligand density per volume of matrix can be optimized to promote target accessibility and binding.

The coupling can be carried out via common functional groups, including amines, alcohols, carboxylic acids, aldehydes and epoxy groups (FIGS. 6A and 6B). Methods of preparing supports according to the invention are known in the art and are described, for example, in U.S. Pat. No. 8,142,844 B2, US 2015/0111194 A1 and US 2014/0166580 A1. These references also describe spacer groups (or "linker" groups) which can be used in generating the matrix according to the invention.

According to one embodiment of the invention, the ligand (PR3) is coupled directly or under addition of a spacer via an amine function. In a first step, an amine group is introduced onto the support. Many methods can be used for introducing amine groups to substrates according to the invention. For example, addition of aminated polymers (e.g. aminated polyvinylalcohols) to the polymer solution prior to membrane precipitation, or post-treatment of membranes such as silanization of a membrane containing hydroxyl or/and carboxyl groups using APTMS ((3-aminopropyl) trimethoxysilane-tetramethoxysilane), simple adsorption of PEI (poly(ethylene imine)) or other polymers onto the membrane surface, or plasma treatment of the membranes with ammonium or other organic amine vapors can effectively be used to introduce amine groups onto membranes. In a second step, carbodiimide compounds can be used to activate carboxylic groups of proteins for direct conjugation to the primary amines on the membrane surface via amide bonds. The most commonly used carbodiimides are the water-soluble EDC (1-ethyl-3-(–3-dimethylaminopropyl) carbodiimide) for aqueous crosslinking and the water-insoluble DCC (N', N'-dicyclohexyl carbodiimide) for non-aqueous organic synthesis methods. According to another embodiment of the invention, hydroxyl groups can be introduced to the support. Substrates based on polysaccharides, for example cellulose or cellulose derivatives, already carry OH-groups on the surface. Hydroxy groups can also be introduced to the substrate for example by plasma treatment with oxygen or air. After acylation of the hydroxy group with succinic anhydride the resulting O-succinate can react with amine of the protein with amide bond formation in the presence of carbodiimide or other coupling reagents. According to yet another embodiment of the invention, carboxylic acid groups can be introduced to the support. Carboxylate groups can be introduced on substrates by plasma treatment with carbon dioxide. For protein immobilization carbodiimide/succinimide coupling chemistry can be used for surface attachment via amine group of the ligand. According to yet another embodiment of the invention, carbonyl groups (aldehydes, ketones) can be introduced for the subsequent coupling of a ligand. Aldehydes can be created on polysaccharide-based solid substrates by oxidation of OH-groups using periodic acid. The primary amines of proteins (N-terminus of polypeptides and the side chain of lysines) can react with aldehydes via reductive amination and formation of a Schiff base. The Schiff base formed then hydrolyzes in an aqueous solution and must be reduced to an alkylamine linkage for stabilization. Sodium cyanoborohydride is a mild reducing agent that induces this reaction without also reducing other chemical groups of proteins. According to still another embodiment of the invention, epoxy groups can be introduced to a support. Several pre-activated resins coated with high density epoxy functional groups on the surface are available commercially, see below. The introduction of epoxy groups on membranes is described, for example, in WO 2005/026224 A1. The epoxide group which reacts with nucleophiles in a ring-opening process reacts with primary amines, thiols or hydroxyl groups of proteins to form stable secondary amines, thio-esters and ether bonds, respectively. The epoxide groups readily react with thiol groups and require buffered systems close to physiological pH (pH 7.5-8.5). The epoxide groups require high pH conditions (pH 11-12) for reacting with hydroxyl groups and moderate alkaline conditions (pH >9) for reaction with amine groups. In each case, spacers of varying chain length can be introduced between the support and the affinity ligand.

There are several types of supports as mentioned above and below that can be advantageously utilized to couple, for example, proteins for use in affinity chromatography. Affinity supports can be based on materials such as polysaccharide. Suitable polysaccharides are, for example, cellulose, nitrocellulose, chitosan, collagen, starch and cross-linked polysaccharide gels such as agarose, Sephadex or Sepharose. Methods for preparing derivatives of polysaccharide matrices have long been known and are, for example, described in U.S. Pat. No. 4,411,832 or U.S. Pat. No. 3,947,352. The supports can also be based on synthetic organic supports. Synthetic polymeric matrices comprise hydrophilic and hydrophobic synthetic polymers and combinations thereof. Synthetic supports comprise supports selected, for example, from the group of supports consisting of polyacrylamide supports or derivatives thereof; polymethacrylate supports or derivatives thereof; polystyrene supports or derivatives thereof; or polyethersulfone supports or derivatives thereof. Otherwise, derivatized silica, glass or azlactone beads can be used in devices according to the invention. Such devices preferably make use of organic supports. The use of beads may be advantageous in the context of the present invention.

According to one embodiment of the invention, the support material should be porous, wherein the pore size is in the range of from 10 to 200 nm. For affinity applications the pore size has been found to be optimal in the range of from 30 to 200 nm or in the range of 60 to 200 nm. However, other pore sizes may be advantageous as well depending on the coupling chemistry, spacer and ligand used, and also depending on the target protein. If the support is used in the form of beads, the diameter of such beads may vary of a certain range. It may be advantageous to use beads with a diameter in the range of from 50 to 1000 µm. It may be further advantageous to use beads with a diameter in the range of from 60 to 800 µm, 100 to 700 µm, 120 to 800 µm.

According to one aspect of the present invention, the supports carry specific functional groups which are needed for coupling a linker and/or ligand thereto. For example, many functionalized resins are commercially available and known to a person with skill in the art. Pre-activated resin supports which already carry a reactive group for the coupling of a ligand with or without a spacer are available commercially and eliminate many of the steps of chemical activation of the support prior to use mentioned before, i.e. prior to the coupling of a ligand. Such supports are generally resins as defined before, whereas for membrane and/or non-woven supports the step of activation generally has to be performed before coupling. A wide range of coupling chemistries, involving primary amines, sulfhydryls, aldehydes, hydroxyls and carboxylic acids are available in said commercial supports for covalently attaching ligands. Examples for commercially available activated resins are UltraLink Iodoacetyl resin, CarboLink Coupling resin, Profinity™ Epoxide resin, Affi-Gel 10 and 15, Epoxy-activated Sepharose™ 6B, Tresyl chloride-activated agarose, Tosoh Toyopearl® AF Amino or Epoxy 650-M, ChiralVision Immobead™ 350, Resindion ReliZyme™ EXE 135 or SEPABEADS™ and Purolite® Lifetech™ methacrylate polymers functionalized with epoxy groups.

According to one embodiment of the invention, the support used for the coupling of a ligand (PR3) is epoxy functionalized because epoxy groups form very stable covalent linkages with different protein groups such as, for example, —NH$_2$ in lysine or nucleophiles (amino, thiol, phenolic) and immobilization can be performed under mild conditions of pH and temperature.

According to another embodiment of the invention, the support takes the form of beads. According to yet another embodiment of the invention, the support is an epoxy-functionalized methacrylate polymer. According to yet another embodiment of the invention, the support is selected from the group of supports consisting of Tosoh Toyopearl® Epoxy 650-M, ChiralVision Immobead™ 350, Resindion ReliZyme™ EXE 135, Resindion SEPABEADS™ and Purolite® Lifetech™. According to one aspect, Purolite® Lifetech™ ECR8209F epoxy methacrylate beads are used which carry an epoxy group as a functional group to which a ligand can be bound. They have a mean pore diameter of between 1200 and 1800 Å and a particle size of between 150 and 300 µm. According to another aspect, Purolite® Lifetech™ ECR8215M epoxy methacrylate beads are used which carry an epoxy group as a functional group to which a ligand can be bound. They have a mean pore diameter of between 600 and 1200 Å and a particle size of between 300 and 710 µm. According to another aspect, Purolite® Lifetech™ ECR8215F epoxy methacrylate beads are used which carry an epoxy group as a functional group to which a ligand can be bound. They have a mean pore diameter of between 1200 and 1800 Å and a particle size of between 150 and 300 µm.

According to another embodiment of the invention, it is also possible to immobilize the ligand (PR3) non-covalently to the support, for example ionically or by complexation. However, covalent binding is preferred to avoid the risk of leaching of the ligand from the matrix into the blood or blood plasma of the patient.

According to yet another embodiment, the support according to the invention comprises magnetic beads. Magnetic beads are prepared by entrapping magnetite within agarose or other polymeric material, on which the ligand according to the invention is immobilized. Following the interaction of ligand and target protein, under the influence of a magnet, rapid separation can be achieved. The use of magnetic beads is especially indicated in extracorporeal applications which are in vitro applications and wherein the matrix for immobilizing the target proteins is configured for monitoring the presence and/or concentration of the target proteins in a blood or blood plasma sample or in any other in vitro application comprising the target proteins, for screening or other analytical purposes and is not part of the extracorporeal blood circuit. Following the interaction of ligand and target protein, under the influence of a magnet, rapid separation of the target protein can be achieved.

According to another embodiment of the present invention the support is a membrane. Membranes as components of affinity matrices have been used in protein purification, due to their simplicity, ease of handling, reduced surface area and lower diffusion limitations compared to gels, resins and beads. Membranes have been successfully utilized as affinity membranes for the purification of a recombinant antibodies (Sun et al., J. Sep. Sci., 31 (2008), pp. 1201-1206). Affinity membranes are adaptable to be used in various sizes and formats. The membranes can take the physical form of a hollow fiber or, alternatively, of a flat sheet membrane.

According to one embodiment of the invention, the support membrane is a hollow fiber membrane. According to another embodiment of the invention, a multitude of hollow fiber membranes are formed to a bundle of hollow fibers and embedded in a housing, thus forming a filter or filtration device. According to one embodiment, the support comprises a hemodialysis hollow fiber membrane dialyzer, wherein the filter is a hemodialyzer.

Such an embodiment provides a combination of two functions and can be advantageously utilized as a device for removal of ANCA from the blood or blood plasma of a person in need in an extracorporeal blood circuit, wherein the device comprises a matrix configured to immobilize ANCA via binding to monomeric PR3, because the device simultaneously removes a target protein according to the invention and removes uremic toxins, excess ions and water from the blood of the patient who suffers from renal failure. Accordingly, only one device is needed for the treatment of a patient suffering from an ANCA-related disease. An extracorporeal circuit is accordingly not basically different from a standard extracorporeal circuit for performing hemodialysis in the treatment of renal failure. The treatment of such patients suffering from renal failure and an ANCA-related disease is thus significantly simplified and may help to reduce costs for the cumulative treatment of the patients and increase the treatment options for the patients and attending physicians.

The hollow fiber or flat sheet membranes for use as supports in a device according to the invention may be composed of cellulose, cellulose ester (cellulose acetate and cellulose triacetate), poly(methylmethacrylate)(PMMA), polyamide (PA), other nitrogen-containing polymers (polybenzimidazole, polyacrylonitrile (PAN), polyglycidyl methacrylate (PGMA), polyvinylpyrrolidone (PVP), polysulfone (PS), polyethersulfone (PES), polyarylethersulfone (PAES), combinations of said polymers and any of these polymers modified by introduction of functional groups. According to one embodiment of the invention, the membrane supports according to the invention comprise a polymer selected from the group of polymers consisting of poly(methylmethacrylate) (PMMA), polyamide (PA), polyacrylonitrile (PAN), polyvinylpyrrolidone (PVP), polysulfone (PS), polyethersulfone (PES), polyarylethersulfone (PAES), combinations of said polymers and any of these polymers modified by introduction of functional groups. According to another embodiment of the invention, the membrane supports according to the invention comprise a polymer selected from the group of polymers consisting of polyamide (PA), polyacrylonitrile (PAN), polyvinylpyrrolidone (PVP), polysulfone (PS), polyethersulfone (PES), polyarylethersulfone (PAES), combinations of said polymers and any of these polymers modified by introduction of functional groups. According to yet another embodiment of the invention, the membrane supports according to the invention comprise a polymer selected from the group of polymers consisting of polyvinylpyrrolidone (PVP), polysulfone (PS), polyethersulfone (PES), and polyarylethersulfone (PAES), combinations of said polymers and any of these polymers modified by introduction of functional groups.

For performing a coupling reaction for the subsequent binding of a ligand (PR3) on the membrane surface, a polymer functionalization step is needed known methods can be used such as described in, for example, US 2015/0111194 A1 and US 2014/0166580 A1. For example, a synthetic material made of an alkane chain like, e.g., polyethylene, does not comprise suitable functional groups for coupling a molecule thereto. Therefore, suitable functional groups have to be introduced chemically after polymer synthesis. A possibility for modifying a polymer is the known method of plasma functionalization which allows, by selection of suitable gas plasma, to introduce functional groups into polymers. This method comprises, for example, the use of ammonia plasma, wherein amino functions are formed on the surface of the treated polymer. Hence, treatment of e.g. polyethylene with ammonia plasma leads to a polyethylene matrix bearing a certain amount of amino functions. These amino groups may afterwards be reacted with a suitable functional group of the linker, e.g. a carboxyl group. Alternatively, the matrix polymer can be functionalized by plasma activation to obtain carboxylic groups. A method for functionalizing a hollow fiber membrane in a continuous manner is further described, for example, in US 2007/0296105 A1. In said method the functional groups comprised introduced by the precursor gas may be amino, carboxyl, aldehyde, ester, epoxy, hydroxyl or sulphonic acids groups. Membranes which can be used as supports according to the invention comprise, for example, plasma separation membranes and hemodialysis membranes known in the art, including, but not limited to, well known high-flux membranes, high cut-off membranes or medium cut-off membranes. It is the goal of plasma separation to have the total plasma protein of the blood in the separated plasma fraction, whereas the larger corpuscular components of the blood, like blood cells and cell debris, are retained by the membrane. Further, such a plasma separation membrane should exhibit a high surface porosity and total porosity of the membrane to achieve high filtration performance. It should also be characterized by a hydrophilic, spontaneously wettable membrane structure, low fouling properties for long term stable filtration, and low protein adsorption. Such a plasma separation membrane preferably has smooth surfaces in contact with blood, thus avoiding or minimizing hemolysis during blood processing. The membrane should show constant sieving properties and filtration behavior over the whole treatment period. It should further exhibit high biocompatibility, low or no complement activation and low thrombogenicity. Membranes suitable for plasma separation which can be used for providing a device according to the invention are known in the art and have been described, for example, in EP 1 875 956 A1 or EP 1 875 957 A1. Other membranes which can be modified and used as supports in devices according to the invention, such as high-flux membranes as used, for example, in the Revaclear® dialyzer, have been described in EP 2 113 298 B1. Medium cut-off membranes as used, for example, in the Theranova® dialyzer have been described US 2017/0165616 A1 and high cut-off membranes as used, for example, in the Theralite® dialyzer, have been described in EP 1 572 330 A1.

According to one embodiment of the invention, the device according to the invention comprises hollow fiber membranes selected from a group of hemodialysis hollow fiber membranes prepared from polysulfone, polethersulfone or polyarylethersulfone and polyvinylpyrrolidone.

A hollow fiber membrane which can advantageously be utilized for providing a device according to the invention preferably has an inner diameter in the range of 100 to 500 µm. According to one embodiment of the present invention the hollow fiber membrane has a wall thickness in the range of from 20 to 150 µm. Lower wall thicknesses are disadvantageous due to reduced mechanical properties of the fiber during production and during its use in the device according to the invention itself. Higher wall thicknesses are disadvantageous because they require increased time intervals to perform the phase inversion process resulting in instable process conditions and an instable membrane.

In one embodiment of the invention, wherein the membrane used for providing a device according to the invention is a plasma separation membrane or is otherwise configured to allow the passage of the target protein according the invention to a significant amount with a sieving coefficient of higher than 0.5 and preferably higher than 0.7 or higher than 0.9, the inner layer or lumen of the hollow fibers which generally is the blood contacting layer, is not functionalized and does not carry any ligand. The ligand (PR3) is instead coupled via a linker to the outer layer of the hollow fibers, and optionally also to at least a portion of the layer connecting the inner layer with the outer layer, i.e. the pores of the membrane. Accordingly, the functionalization with ligands is present only on the outer filtrate layer and optionally on at least a portion of the pore surface structures connecting the outer and inner layer of the membrane. Such configuration can be applied, for example, for the removal of the target proteins from whole blood which due to their size are able to pass from the inner layer to the outer layer, while larger blood proteins remain on the lumen side of the membrane. As blood components including the target proteins are passaging to the outer layer of the membrane they are immobilized on or bound by the specific ligand.

According to another embodiment of the invention, specifically when the membrane support is a hemodialysis membrane as described above, the hollow fiber membranes are additionally or alternatively functionalized with a ligand according to the invention on the lumen side of the hollow fibers where they can directly interact with and bind or immobilize the target protein comprised in the blood or blood plasma which perfuses the lumen of the hollow fiber membrane.

Another aspect of the invention is a blood treatment device comprising a membrane which is functionalized according to the invention with ligand (monomeric PR3) that is configured to bind or immobilize a target protein (ANCA). Examples of such devices are dialyzers, hemofilters, and ultrafilters. Such devices generally consist of a housing comprising a tubular section with end caps. A bundle of hollow fiber membranes is usually arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2.

According to another aspect, the device according to the invention can be a filter device as disclosed in WO 2014/07680 A1, which comprises both a bundle of hollow fiber membranes and a resin in the filtrate space of the device, wherein the resin preferably consists of beads. Such device can be configured in a way to serve as a device for removing a target protein according to the present invention by selecting a membrane which allows the passage of at least the relevant target protein through the membrane wall. The resin in the filtrate space of the device serves as the matrix and comprises a resin support, such as disclosed herein or in WO 2014/07680 A1 to which the ligand having an affinity to the target protein is bound by methods disclosed herein or as otherwise known in the art.

According to one aspect, the hollow fiber membrane of said device is a plasma separation membrane which allows passage of the blood plasma together with the target proteins contained therein to pass the membrane and interact with the matrix in the filtrate space, thereby allowing the target proteins to be immobilized on the matrix. The cleansed plasma will reenter the hollow fiber membranes within the same device and the blood can return to the patient. Such a device can be located in the extracorporeal circuit either upstream or downstream of a hemodialyzer, such as described in WO 2014/079681 A2, or it can be used as a sole hemoperfusion device within the circuit. In another aspect, the ligand can also or exclusively be bound to the plasma separation membrane as described above, for example to the outside and/or pores of the membrane. The resin in the filtrate space can, in one aspect, be configured to remove the same or a different target protein.

According to yet another embodiment of the invention, the support is a non-woven. The expression "non-woven" as used herein refers to a material which is broadly defined as a sheet, fabric or web structure bonded together by entangling fiber or filaments (and by perforating films) mechanically, thermally, or chemically but not by weaving or knitting. They form porous structures which can efficiently be used as a support material in devices according to the invention due to their high filtration efficiency, high surface area and high permeability. Nonwovens and processes for their production, comprising melt-blown non-wovens and spunlaid nonwovens, as well as devices containing such non-wovens are known in the art and have been described, for example, in EP 1 922 097 A1, WO 2007/025738 A2 and in Zhao et al., J Mem Sci (2011), 369: 5-12. Non-wovens can be composed of biopolymers selected from the group consisting of polysaccharides, polylactic acids (PLA), polycaprolactone (PCL) and proteins, from inorganic materials selected from the group consisting of $TiO_2$, $SiO_2$ or $AlO_2$, or from synthetic polymers selected from the group consisting of polypropylene(PP), polyethylene(PE), polyacrylonitrile (PAN), Poly(vinyl alcohol)(PVA), polyamide-imide (PAI), polyurethane (PUR), polyethersulfone (PES), polyacrylic acid (PAA), polyethylene oxide (PEO), polystyrene (PS) and polyvinylidene fluoride (PVDF).

Typically, devices according to the invention are designed as cylinders with a cylindrical housing having at least one inlet and at least one outlet for the blood or blood plasma which is treated with it. Where the device is a hemodialyzer which in addition to the removal of at least one target protein serves for the treatment of renal failure in HD, HDF or HF, the device further comprises an inlet and an outlet for dialysis fluid. Device configurations which can be used according to the invention are generally known and are within the scope of this invention.

According to the invention, the expression "extracorporeal blood purification" refers to the process of removing substances from body fluids through their clearance from flowing blood in a diverted circuit outside the patient's body (extracorporeal). Said substances may include endogenous toxins (i.e., uremic toxins), exogenous poisons (i.e., ethylene glycol or fungal toxin), administered drugs, viruses, bacteria, antibodies and proteins (i.e., IMHA, myasthenia gravis), abnormal cells (i.e., leukemia), and excessive water. Therapeutic procedures include hemodialysis, including intermittent hemodialysis (HD, HDF, HF) and continuous renal replacement therapy (CRRT); hemoperfusion; and therapeutic apheresis.

According to one aspect, blood flow rates in an extracorporeal blood purification circuit are between 20 ml and 700 ml/min. Typical dialysate flow rates in an extracorporeal circuit comprising a hemodialyzer for the treatment of renal failure either in addition to the blood treatment device according to the invention or in cases where the hemodialyzer in addition is configured to immobilize a target protein is in the range of between 0.5 l/h and 800 ml/min.

In hemodialysis, blood is circulated in an extracorporeal circuit and its composition is modified by the mass transfer of solute and water by diffusive and/or convective forces across an interfacing semipermeable membrane. The magnitude and spectrum of the solute transfer is predicated on the nature of the force(s) imposed across the membrane, on the chemical and physical characteristics of the solute, especially also including size, and the structural properties of the membrane. Hemodialysis is a standard treatment for patients suffering from renal failure.

Hemoperfusion is an adsorptive extracorporeal therapy used to manage endogenous and exogenous intoxications that cannot be cleared efficiently by hemodialysis. Adsorption is the principle of molecular attachment of a solute, such a protein, to a material surface (a matrix). In contrast to the physical separation between blood and dialysate that occurs during hemodialysis, during hemoperfusion blood is exposed directly to an adsorbent with the capacity to selectively or non-selectively bind solutes within the blood path.

In therapeutic apheresis blood is separated into its component fractions, for example by centrifugation or by means of a plasma membrane or filter, and the fraction containing the solute which shall be removed, generally the plasma fraction, is specifically treated prior to return to the patient. The present invention provides for an apheresis treatment in which plasma (containing the target proteins) is removed from the patient's flowing blood and, after having been contacted with a device or matrix according to the invention is returned to the patient (FIG. 5). Typical plasma flow rates in an extracorporeal circuit wherein the blood treatment device is perfused with blood plasma is in the range of between 7 ml/min and 250 ml/min.

According to one aspect, the extracorporeal blood circuit according to the invention is configured to perform hemodialysis. In this case, the device according to the invention is, for example, a hemodialyzer which additionally has been configured to immobilize a target protein according to the invention. The circuit can be operated in different treatment modes depending on the medical need, including hemodialysis, hemodiafiltration, hemofiltration mode.

According to one aspect, the extracorporeal blood circuit according to the invention is configured to provide continuous renal replacement therapy (CCRT). Continuous renal replacement therapies (CRRT) are slow dialysis treatments that are provided as a continuous 24 hour per day therapy, mostly to critically ill patient in an ICU setting. Like in intermittent HD for chronic renal failure patients, solute removal with CRRT is achieved either by convection (hemofiltration), diffusion (hemodialysis), or a combination of both these methods (hemodiafiltration). This process requires the use of replacement fluid to prevent iatrogenic acidosis and electrolyte depletion as well as excessive fluid removal. CRRT and how to use it is known in the art.

According to another aspect, the extracorporeal blood circuit according to the invention is configured to perform hemoperfusion. Accordingly, the blood treatment device according to the invention is perfused with whole blood and is located within an extracorporeal circuit (FIG. 3). According to one aspect of the invention, the device is a cartridge comprising a membrane, non-woven or resin to which ligands having an affinity for a target protein have been bound. According to one aspect, when the cartridge's matrix comprises a bundle of hollow fiber membrane to which a ligand having affinity to a target protein is bound (a filter device), the treatment mode can be hemoperfusion with closed dialysate/filtrate ports. According to yet another aspect, the cartridge can be located downstream or upstream of a hemodialyzer which is configured to perform hemodialysis on the blood of a patient (FIGS. 4A and 4B) and can be operated in different treatment modes selected from hemodialysis, hemodiafiltration and hemofiltration.

According to one aspect, the blood treatment device is a filter comprising both hollow fibers and a resin in the filtrate space of the filter as described above. The filter can be operated in hemoperfusion mode or, if combined with a hemodialyzer which can be located upstream or downstream of the device according to the invention, the treatment mode can be hemodialysis, hemodiafiltration or hemofiltration.

According to yet another embodiment of the invention, the devices according to the invention may be regenerated in between treatments.

EXAMPLES

The invention is further described by the following examples. These are intended to present support for the workability of a number of preferred non-limiting embodiments or aspects of the invention without limiting the scope of the invention described herein.

Example 1: Production of Monomer PR3 Protein Variants

Monomeric PR3 protein variants were created essentially as described in Jerke et al (2017, Scientific Reports 7:43328). The proteins were produced from plasmid pTT5 as C-terminal fusions with a human Ig1 Fc, secreted from 293_6E EBNA cells (NRC, Canada) via an N-terminal Ig1 secretion signal peptide and purified from the culture supernatant by passage over immobilized Protein A. Protein A eluted material was immediately neutralized with 1 M HEPES pH 7.5 and Fc removed by addition of TEV protease and incubation overnight at 4° C. The flowthrough of a subsequent Protein A trap column was concentrated and passed over a Superdex 200 size exclusion in 20 mM HEPES, 150 mM NaCl, pH 7.5 for CD177 and in the same buffer plus 0.02% LM for PR3 variants. PR3 variants were activated by enterokinase removal of an N-terminal FLAG peptide and passage over anti-M2 agarose.

Example 2: Comparison of wtPR3 and Monomeric PR3 Properties by Size Exclusion Chromatography PR3 proteins obtained as described above were assessed using size exclusion chromatography for molecular weight. PR3 proteins were diluted in suitable buffer (500 µl @ 1.2 mg/ml, 20 mM HEPES, 150 mM NaCl, 0.02% lauryl-maltoside, pH 7.4), passed through a 0.45 µm filter and subsequently applied to a Superdex S200 gel filtration column at a flow rate of 0.5 ml/min, at 4 degrees C. and applied to a gel filtration column. High molecular weight aggregates of wtPR3 eluted at approx. 8.8 mL elution volume (FIG. 1A), whereas the Trp222Ala PR3 variant eluted primarily at approx. 16.5 mL elution volume, consistent with a monomeric form of the protein (FIG. 1B). Similar results are obtained for Ile221Ala, Ile221Ala+Trp222Ala, Ile221Ala+Ser203Ala, and Ile221Ala+Trp222Ala+Ser203Ala. Further PR3 mutants are being assessed.

Example 3: Comparison of wtPR3 and Monomeric PR3 Properties by SPR

Experiments were performed on a ProteOn XPR36 instrument (BioRad) with proteins immobilized to GLH sensor chips (BioRad) using standard amine chemistry. The binding interaction of a concentration series of soluble monomeric Trp222Ala PR3 variant with immobilized CD177 was assessed (FIG. 2A). The affinity of the interaction was measured to be $5.7 \times 10^{-8}$ M, indicating that the PR3 variant shows no loss in biding to its natural protein target CD177.

Example 4: Comparison of wtPR3 and Monomeric PR3 Properties by ELISA

PR3 ELISA was used to quantitatively assess PR3 amounts. Briefly, anti-PR3 capture antibodies (anti-PR3 40 and anti-PR3 81) were coated, blocked and incubated with PR3 samples of WT or monomeric variants. After washing, biotinylated anti-PR3 detection mab was added. A streptavidin-HRPO conjugate and OPD substrate were used to visualize binding. The absorbance was determined at 405 nm in a plate reader. FIG. 2B shows that wtPR3 (left bar) and the monomeric Trp222Ala PR3 variant (right bar) are equally well recognized by the antibodies.

Example 5: Preparation of a Matrix Comprising an Epoxy-Functionalized Resin

First, the resin is equilibrated. The resin is washed with immobilization buffer and filtered. A resin/buffer ratio of 1/1 (w/v) is preferable. The immobilization buffer is chosen to be compatible with PR3. The process is repeated 2-4 times. The PR3 solution is prepared by dissolving the protein in immobilization buffer. For example, 100-200 mg PR3 can be loaded per gram of wet resin. Protein concentration can be determined by using standard protein content assays. The PR3 is dissolved in a sufficient amount of buffer to obtain a ratio resin/buffer of 1:4 (w/v). This ratio can be optimized depending on the PR protein used (range can vary from 1:1-1:4). Immobilization begins with the transfer of the immobilization buffer containing the PR3 protein into the immobilization vessel. The epoxy-functionalized resin, for example the Purolite® Lifetech™ resin described herein, is then added. The slurry is gently mixed at 70-80 rpm for 18 h and afterwards left without mixing for another 20 h. Magnetic stirring during protein immobilization should be avoided as this can damage the beads. Immobilization can be performed at temperatures of 20° C.-30° C., depending on the protein stability. Immobilizations should not be performed at high temperatures as this can cause degradation of the epoxy rings (hydrolysis) and facilitate microbial growth. Finally, the liquid phase is filtered off and collected. The protein content in the liquid is determined and the immobilization yield calculated. The resin is then washed with washing buffer. The process is repeated 2-4 times under gentle stirring or in column wash. An additional washing step using a 0.5 M NaCl containing buffer for complete desorption of non-covalently bound proteins can be performed. Excess water is removed by filtration. The immobilized PR3 protein can then be characterized in terms of moisture content and specific binding activity.

Example 6: Preparation of a Matrix Comprising an Epoxy-Functionalized Resin

First, the resin is equilibrated. The resin is washed with immobilization buffer and filtered. A resin/buffer ratio of 1:1 (w/v) is preferable. The immobilization buffer is chosen to be compatible with the PR3 protein. In a second step 2% glutaraldehyde buffer is prepared starting from a solution of 25% (w/v) glutaraldehyde. A 2% glutaraldehyde (v/v) solution is prepared using the immobilization buffer. In a third step, the amino resin is activated by adding the 2% glutaraldehyde buffer prepared in step 2 to the resin. The optimal volume of 2% glutaraldehyde buffer should be in the range of resin/buffer ratio of 1:4 (w/v). The slurry is left to mix for 60 min at 20° C.-25° C. The beads are then filtered and washed with immobilization buffer using a resin/buffer ratio of 1:4 (w/v). It should be avoided to store pre-activated resin for a period longer than 48 h. Beads are then ready for the immobilization step. In a fourth step the PR3 protein solution is prepared. To that end, the protein is dissolved in immobilization buffer. For example, between 1 mg and 100 mg PR3 protein can be loaded per gram of wet resin. The protein concentration can be determined by using standard protein content assays.

The protein is dissolved in buffer to obtain a ratio resin/buffer of 1:4 (w/v). Optimization of this ratio can be pursued in further trials (range can vary from 1:1-1:4). In a fifth step, the protein is immobilized. The immobilization buffer is transferred into the immobilization vessel and the pre-activated amino resin (e.g. from Purolite®, Lifetech™) as prepared in step 3 is added. The slurry is gently mixed for 18 h at 70-80 rpm. Magnetic stirring should be avoided during immobilization as this can damage the beads. The immobilization can be performed at 20° C.-30° C. accordingly to PR3 protein stability. The immobilization should not be performed at high temperatures since this might cause side reactions of the aldehyde groups on the resin formed during step 3. Finally, the liquid phase is filtered off and collected. The protein content in the liquid is determined and the immobilization yield calculated. The resin is then washed with washing buffer. The process is repeated 2-4 times under gentle stirring or in column wash. An additional washing step using a 0.5 M NaCl containing buffer for complete desorption of non-covalently bound proteins can be performed. Excess water is removed by filtration. The immobilized PR3 protein can then be characterized in terms of moisture content and specific binding activity.

The invention claimed is:

1. A blood treatment device configured to remove anti-neutrophil cytoplasmic antibodies (ANCAs) from the blood or blood plasma of a person in need thereof in an extracorporeal blood circuit, wherein the device comprises a matrix, and wherein said matrix comprises a monomeric form of proteinase 3 (PR3).

2. The blood treatment device according to claim 1, wherein the monomeric form of proteinase 3 (PR3) comprises at least one mutation at Ile221 and/or Trp222.

3. The blood treatment device according to claim 1, wherein the monomeric form of proteinase 3 (PR3) comprises at least mutations at Ile221 and Trp222.

4. The blood treatment device according to claim 1, wherein the monomeric form of proteinase 3 (PR3) comprises the Ile221Ala and/or Trp222Ala mutations.

5. The blood treatment device according to claim 1, wherein the monomeric form of proteinase 3 (PR3) comprises a mutation that reduces or abolishes protease activity.

6. The blood treatment device according to claim 1, wherein the matrix comprises a support to which the monomeric form of proteinase 3 (PR3) is bound.

7. The blood treatment device according to claim 5, wherein the mutation that reduces or abolishes protease activity is selected from one or more mutations in the group consisting of His71, Asp118 and/or Ser203.

8. The blood treatment device according to claim 7, wherein the mutation that reduces or abolishes protease activity is His71Glu, Asp118Ala and/or Ser203Ala.

9. The blood treatment device according to claim 6, wherein the support comprises or consists of a material selected from the group consisting of hollow fiber membrane, flat sheet membrane, fiber mat, resin, non-woven and open porous foams.

10. The blood treatment device according to claim 9, wherein the support comprises or consists of polyurethane (PU) foam.

11. The blood treatment device according to claim 1, wherein the blood treatment device is an adsorption cartridge and is perfused with whole blood.

12. The blood treatment device according to claim 1, wherein the blood treatment device is located in an extracorporeal blood circuit through which the blood of the patient passes and which is configured for transporting blood from the patient's vascular system to the blood treatment device at a defined flow rate and for returning the treated blood back to the patient.

13. The blood treatment device according to claim 12, wherein the extracorporeal blood circuit in which the blood treatment device is located further comprises a hemodialyzer which is located upstream or downstream of the blood treatment device.

14. The blood treatment device according to claim 12, wherein the extracorporeal blood circuit in which the blood treatment device is located further comprises a plasma dialyzer or centrifuge-based plasma separation system which allows for the separation of a plasma fraction from the blood, and wherein the blood treatment device is located downstream of the plasma outlet port of the plasma dialyzer.

15. An extracorporeal blood circuit comprising a blood treatment device according to claim 1, wherein the extracorporeal blood circuit comprises means for transporting blood or blood plasma from the patient's vascular system to the blood treatment device at a defined flow rate and means for returning the treated blood or blood plasma back to the patient.

16. The extracorporeal blood circuit according to claim 15, wherein the extracorporeal blood circuit further comprises a hemodialyzer for the hemodialysis of blood, wherein the hemodialyzer is located upstream or downstream of the blood treatment device.

17. The extracorporeal blood circuit according to claim 15, wherein said extracorporeal blood circuit further comprises a plasma dialyzer or centrifuge-based plasma separation system configured to separate blood plasma from blood, wherein the blood plasma is passed through the blood treatment device, wherein the blood treatment device is located downstream of the plasma outlet port of the plasma dialyzer.

18. The blood treatment device according to claim 15, wherein the blood treatment device is a hemodialyzer for the hemodialysis of blood, and wherein the hemodialyzer comprises a monomeric form of proteinase 3 (PR3) and is configured to immobilize anti-neutrophil cytoplasmic antibodies (ANCAs).

19. The blood treatment device according to claim 15, wherein the blood treatment device is a plasma dialyzer configured to separate blood plasma from blood, and wherein the plasma dialyzer comprises a monomeric form of proteinase 3 (PR3) and is configured to immobilize anti-neutrophil cytoplasmic antibodies (ANCAs).

20. The blood treatment device according to claim 15, wherein the autoimmune disease associated with the presence of anti-PR3 autoantibodies is an anti-neutrophil cytoplasmic antibody (ANCA) vasculitides, pauci-immune crescentic glomerulonephritis or eosinophilic granulomatosis with polyangiitis.

21. The blood treatment device according to claim 20, wherein the anti-neutrophil cytoplasmic antibody (ANCA) vasculitides is a granulomatosis with polyangiitis or microscopic polyangiitis.

22. A method of treating a medical condition associated with anti-neutrophil cytoplasmic antibodies (ANCA), said method comprising removing anti-neutrophil cytoplasmic antibodies (ANCAs) from the blood or blood plasma of a person in need thereof using the blood treatment device according to claim 1.

23. The method of treatment according to claim 22, wherein the medical condition associated with anti-neutrophil cytoplasmic antibodies (ANCAs) is an autoimmune disease associated with the presence of anti-PR3 autoantibodies.

24. The method of treatment according to claim 22, wherein the medical condition associated with anti-neutrophil cytoplasmic antibodies (ANCAs) is anti-neutrophil cytoplasmic autoantibody (ANCA)-associated autoimmune vasculitis (AAV).

* * * * *

```
                            SEQUENCE LISTING

<160> NUMBER OF SEQ ID NOS: 7

<210> SEQ ID NO 1
    <211> LENGTH: 256
    <212> TYPE: PRT
    <213> ORGANISM: Homo sapiens

<400> SEQUENCE: 1

Met Ala His Arg Pro Pro Ser Pro Ala Leu Ala Ser Val Leu Leu Ala
    1               5                   10                  15

Leu Leu Leu Ser Gly Ala Ala Arg Ala Ala Glu Ile Val Gly Gly His
                    20                  25                  30

Glu Ala Gln Pro His Ser Arg Pro Tyr Met Ala Ser Leu Gln Met Arg
                35                  40                  45

Gly Asn Pro Gly Ser His Phe Cys Gly Gly Thr Leu Ile His Pro Ser
            50                  55                  60

Phe Val Leu Thr Ala Ala His Cys Leu Arg Asp Ile Pro Gln Arg Leu
    65                  70                  75                  80

Val Asn Val Val Leu Gly Ala His Asn Val Arg Thr Gln Glu Pro Thr
                    85                  90                  95

Gln Gln His Phe Ser Val Ala Gln Val Phe Leu Asn Asn Tyr Asp Ala
                100                 105                 110

Glu Asn Lys Leu Asn Asp Val Leu Leu Ile Gln Leu Ser Ser Pro Ala
                115                 120                 125

Asn Leu Ser Ala Ser Val Ala Thr Val Gln Leu Pro Gln Gln Asp Gln
            130                 135                 140

Pro Val Pro His Gly Thr Gln Cys Leu Ala Met Gly Trp Gly Arg Val
    145                 150                 155                 160

Gly Ala His Asp Pro Pro Ala Gln Val Leu Gln Glu Leu Asn Val Thr
                    165                 170                 175

Val Val Thr Phe Phe Cys Arg Pro His Asn Ile Cys Thr Phe Val Pro
                180                 185                 190

Arg Arg Lys Ala Gly Ile Cys Phe Gly Asp Ser Gly Gly Pro Leu Ile
                195                 200                 205

Cys Asp Gly Ile Ile Gln Gly Ile Asp Ser Phe Val Ile Trp Gly Cys
            210                 215                 220

Ala Thr Arg Leu Phe Pro Asp Phe Phe Thr Arg Val Ala Leu Tyr Val
    225                 230                 235                 240

Asp Trp Ile Arg Ser Thr Leu Arg Arg Val Glu Ala Lys Gly Arg Pro
                    245                 250                 255
```

<210> SEQ ID NO 2
<211> LENGTH: 256
<212> TYPE: PRT
<213> ORGANISM: Artificial Sequence
<220> FEATURE:
<223> OTHER INFORMATION: variant
<220> FEATURE:
<221> NAME/KEY: misc_feature
<222> LOCATION: (221)..(221)
<223> OTHER INFORMATION: Xaa can be any naturally occurring amino acid

<400> SEQUENCE: 2

Met Ala His Arg Pro Pro Ser Pro Ala Leu Ala Ser Val Leu Leu Ala
1               5                   10                  15

Leu Leu Leu Ser Gly Ala Ala Arg Ala Ala Glu Ile Val Gly Gly His
            20                  25                  30

Glu Ala Gln Pro His Ser Arg Pro Tyr Met Ala Ser Leu Gln Met Arg
        35                  40                  45

Gly Asn Pro Gly Ser His Phe Cys Gly Gly Thr Leu Ile His Pro Ser
    50                  55                  60

Phe Val Leu Thr Ala Ala His Cys Leu Arg Asp Ile Pro Gln Arg Leu
65                  70                  75                  80

Val Asn Val Val Leu Gly Ala His Asn Val Arg Thr Gln Glu Pro Thr
                85                  90                  95

Gln Gln His Phe Ser Val Ala Gln Val Phe Leu Asn Asn Tyr Asp Ala
            100                 105                 110

Glu Asn Lys Leu Asn Asp Val Leu Leu Ile Gln Leu Ser Ser Pro Ala
        115                 120                 125

Asn Leu Ser Ala Ser Val Ala Thr Val Gln Leu Pro Gln Gln Asp Gln
    130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
            180                 185                 190

Arg Arg Lys Ala Gly Ile Cys Phe Gly Asp Ser Gly Gly Pro Leu Ile
        195                 200                 205

Cys Asp Gly Ile Ile Gln Gly Ile Asp Ser Phe Val Xaa Trp Gly Cys
    210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

<210> SEQ ID NO 3
<211> LENGTH: 256
<212> TYPE: PRT
<213> ORGANISM: Artificial Sequence
<220> FEATURE:
<223> OTHER INFORMATION: variant
<220> FEATURE:
<221> NAME/KEY: misc_feature
<222> LOCATION: (221)..(222)
<223> OTHER INFORMATION: Xaa can be any naturally occurring amino acid

<400> SEQUENCE: 3

Met Ala His Arg Pro Pro Ser Pro Ala Leu Ala Ser Val Leu Leu Ala
1               5                   10                  15

```
Leu Leu Leu Ser Gly Ala Ala Arg Ala Ala Glu Ile Val Gly Gly His
             20                  25                  30

Glu Ala Gln Pro His Ser Arg Pro Tyr Met Ala Ser Leu Gln Met Arg
         35                  40                  45

Gly Asn Pro Gly Ser His Phe Cys Gly Thr Leu Ile His Pro Ser
 50                  55                  60

Phe Val Leu Thr Ala Ala His Cys Leu Arg Asp Ile Pro Gln Arg Leu
 65                  70                  75                  80

Val Asn Val Val Leu Gly Ala His Asn Val Arg Thr Gln Glu Pro Thr
                 85                  90                  95

Gln Gln His Phe Ser Val Ala Gln Val Phe Leu Asn Asn Tyr Asp Ala
             100                 105                 110

Glu Asn Lys Leu Asn Asp Val Leu Leu Ile Gln Leu Ser Ser Pro Ala
         115                 120                 125

Asn Leu Ser Ala Ser Val Ala Thr Val Gln Leu Pro Gln Gln Asp Gln
 130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                 165                 170                 175

Val Val Thr Phe Phe Cys Arg Pro His Asn Ile Cys Thr Phe Val Pro
             180                 185                 190

Arg Arg Lys Ala Gly Ile Cys Phe Gly Asp Ser Gly Gly Pro Leu Ile
         195                 200                 205

Cys Asp Gly Ile Ile Gln Gly Ile Asp Ser Phe Val Xaa Xaa Gly Cys
 210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                 245                 250                 255

<210> SEQ ID NO 4
<211> LENGTH: 256
<212> TYPE: PRT
<213> ORGANISM: Artificial Sequence
<220> FEATURE:
<223> OTHER INFORMATION: variant
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid

<400> SEQUENCE: 4

Met Ala His Arg Pro Pro Ser Pro Ala Leu Ala Ser Val Leu Leu Ala
 1               5                  10                  15

Leu Leu Leu Ser Gly Ala Ala Arg Ala Ala Glu Ile Val Gly Gly His
             20                  25                  30

Glu Ala Gln Pro His Ser Arg Pro Tyr Met Ala Ser Leu Gln Met Arg
         35                  40                  45
```

```
Gly Asn Pro Gly Ser His Phe Cys Gly Gly Thr Leu Ile His Pro Ser
        50                  55                  60

Phe Val Leu Thr Ala Ala Xaa Cys Leu Arg Asp Ile Pro Gln Arg Leu
 65                  70                  75                  80

Val Asn Val Val Leu Gly Ala His Asn Val Arg Thr Gln Glu Pro Thr
                 85                  90                  95

Gln Gln His Phe Ser Val Ala Gln Val Phe Leu Asn Asn Tyr Asp Ala
                100                 105                 110

Glu Asn Lys Leu Asn Xaa Val Leu Leu Ile Gln Leu Ser Ser Pro Ala
            115                 120                 125

Asn Leu Ser Ala Ser Val Ala Thr Val Gln Leu Pro Gln Gln Asp Gln
        130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
                180                 185                 190

Arg Arg Lys Ala Gly Ile Cys Phe Gly Asp Xaa Gly Gly Pro Leu Ile
            195                 200                 205

Cys Asp Gly Ile Ile Gln Gly Ile Asp Ser Phe Val Xaa Trp Gly Cys
210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

<210> SEQ ID NO 5
<211> LENGTH: 256
<212> TYPE: PRT
<213> ORGANISM: Artificial Sequence
<220> FEATURE:
<223> OTHER INFORMATION: variant
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (221)..(222)
<223> OTHER INFORMATION: Xaa can be any naturally occurring amino acid

<400> SEQUENCE: 5

Met Ala His Arg Pro Pro Ser Pro Ala Leu Ala Ser Val Leu Leu Ala
  1               5                  10                  15

Leu Leu Leu Ser Gly Ala Ala Arg Ala Ala Glu Ile Val Gly Gly His
                 20                  25                  30

Glu Ala Gln Pro His Ser Arg Pro Tyr Met Ala Ser Leu Gln Met Arg
             35                  40                  45

Gly Asn Pro Gly Ser His Phe Cys Gly Gly Thr Leu Ile His Pro Ser
         50                  55                  60

Phe Val Leu Thr Ala Ala Xaa Cys Leu Arg Asp Ile Pro Gln Arg Leu
```

-continued

```
                65                  70                  75                  80
    Val Asn Val Val Leu Gly Ala His Asn Val Arg Thr Gln Glu Pro Thr
                    85                  90                  95

Gln Gln His Phe Ser Val Ala Gln Val Phe Leu Asn Asn Tyr Asp Ala
                    100                 105                 110

Glu Asn Lys Leu Asn Xaa Val Leu Leu Ile Gln Leu Ser Ser Pro Ala
                    115                 120                 125

Asn Leu Ser Ala Ser Val Ala Thr Val Gln Leu Pro Gln Gln Asp Gln
                    130                 135                 140

Pro Val Pro His Gly Thr Gln Cys Leu Ala Met Gly Trp Gly Arg Val
    145                 150                 155                 160

Gly Ala His Asp Pro Pro Ala Gln Val Leu Gln Glu Leu Asn Val Thr
                    165                 170                 175

Val Val Thr Phe Phe Cys Arg Pro His Asn Ile Cys Thr Phe Val Pro
                    180                 185                 190

Arg Arg Lys Ala Gly Ile Cys Phe Gly Asp Xaa Gly Gly Pro Leu Ile
                    195                 200                 205

Cys Asp Gly Ile Ile Gln Gly Ile Asp Ser Phe Val Xaa Xaa Gly Cys
                    210                 215                 220

Ala Thr Arg Leu Phe Pro Asp Phe Phe Thr Arg Val Ala Leu Tyr Val
    225                 230                 235                 240

Asp Trp Ile Arg Ser Thr Leu Arg Arg Val Glu Ala Lys Gly Arg Pro
                    245                 250                 255

<210> SEQ ID NO 6
<211> LENGTH: 256
<212> TYPE: PRT
<213> ORGANISM: Artificial Sequence
<220> FEATURE:
<223> OTHER INFORMATION: variant

<400> SEQUENCE: 6

Met Ala His Arg Pro Pro Ser Pro Ala Leu Ala Ser Val Leu Leu Ala
    1               5                   10                  15

Leu Leu Leu Ser Gly Ala Ala Arg Ala Ala Glu Ile Val Gly Gly His
                    20                  25                  30

Glu Ala Gln Pro His Ser Arg Pro Tyr Met Ala Ser Leu Gln Met Arg
                    35                  40                  45

Gly Asn Pro Gly Ser His Phe Cys Gly Gly Thr Leu Ile His Pro Ser
                    50                  55                  60

Phe Val Leu Thr Ala Ala His Cys Leu Arg Asp Ile Pro Gln Arg Leu
    65                  70                  75                  80

Val Asn Val Val Leu Gly Ala His Asn Val Arg Thr Gln Glu Pro Thr
                    85                  90                  95

Gln Gln His Phe Ser Val Ala Gln Val Phe Leu Asn Asn Tyr Asp Ala
                    100                 105                 110

Glu Asn Lys Leu Asn Asp Val Leu Leu Ile Gln Leu Ser Ser Pro Ala
                    115                 120                 125

Asn Leu Ser Ala Ser Val Ala Thr Val Gln Leu Pro Gln Gln Asp Gln
                    130                 135                 140

Pro Val Pro His Gly Thr Gln Cys Leu Ala Met Gly Trp Gly Arg Val
    145                 150                 155                 160

Gly Ala His Asp Pro Pro Ala Gln Val Leu Gln Glu Leu Asn Val Thr
                    165                 170                 175

Val Val Thr Phe Phe Cys Arg Pro His Asn Ile Cys Thr Phe Val Pro
```

```
                180                 185                 190
Arg Arg Lys Ala Gly Ile Cys Phe Gly Asp Ala Gly Pro Leu Ile
            195                 200                 205

Cys Asp Gly Ile Ile Gln Gly Ile Asp Ser Phe Val Ala Trp Gly Cys
    210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

<210> SEQ ID NO 7
<211> LENGTH: 256
<212> TYPE: PRT
<213> ORGANISM: Artificial Sequence
<220> FEATURE:
<223> OTHER INFORMATION: variant

<400> SEQUENCE: 7

Met Ala His Arg Pro Pro Ser Pro Ala Leu Ala Ser Val Leu Leu Ala
1               5                   10                  15

Leu Leu Leu Ser Gly Ala Ala Arg Ala Ala Glu Ile Val Gly Gly His
            20                  25                  30

Glu Ala Gln Pro His Ser Arg Pro Tyr Met Ala Ser Leu Gln Met Arg
        35                  40                  45

Gly Asn Pro Gly Ser His Phe Cys Gly Gly Thr Leu Ile His Pro Ser
    50                  55                  60

Phe Val Leu Thr Ala Ala His Cys Leu Arg Asp Ile Pro Gln Arg Leu
65                  70                  75                  80

Val Asn Val Val Leu Gly Ala His Asn Val Arg Thr Gln Glu Pro Thr
                85                  90                  95

Gln Gln His Phe Ser Val Ala Gln Val Phe Leu Asn Asn Tyr Asp Ala
            100                 105                 110

Glu Asn Lys Leu Asn Asp Val Leu Leu Ile Gln Leu Ser Ser Pro Ala
        115                 120                 125

Asn Leu Ser Ala Ser Val Ala Thr Val Gln Leu Pro Gln Gln Asp Gln
    130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
            180                 185                 190

Arg Arg Lys Ala Gly Ile Cys Phe Gly Asp Ala Gly Gly Pro Leu Ile
        195                 200                 205

Cys Asp Gly Ile Ile Gln Gly Ile Asp Ser Phe Val Ala Ala Gly Cys
    210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255
```